(12) United States Patent
Miller

(10) Patent No.: US 11,324,521 B2
(45) Date of Patent: May 10, 2022

(54) APPARATUS AND METHOD TO ACCESS BONE MARROW

(71) Applicant: TELEFLEX LIFE SCIENCES LIMITED, Valletta (MT)

(72) Inventor: Larry J. Miller, Spring Branch, TX (US)

(73) Assignee: TELEFLEX LIFE SCIENCES LIMITED, Valletta (MT)

( * ) Notice: Subject to any disclaimer, the term of this patent is extended or adjusted under 35 U.S.C. 154(b) by 0 days.

(21) Appl. No.: 16/821,627

(22) Filed: Mar. 17, 2020

(65) Prior Publication Data

US 2020/0214722 A1   Jul. 9, 2020

Related U.S. Application Data

(60) Continuation of application No. 16/664,282, filed on Oct. 25, 2019, which is a continuation of application
(Continued)

(51) Int. Cl.
*A61B 17/16* (2006.01)
*A61B 17/34* (2006.01)
(Continued)

(52) U.S. Cl.
CPC ........ *A61B 17/1671* (2013.01); *A61B 10/025* (2013.01); *A61B 10/0283* (2013.01);
(Continued)

(58) Field of Classification Search
CPC ............ A61B 17/1622; A61B 17/1617; A61B 2010/0258; A61B 10/025; A61B 17/3472
See application file for complete search history.

(56) References Cited

U.S. PATENT DOCUMENTS

| 1,272,104 A | 7/1918 | Riethmueller |
| 1,539,637 A | 5/1925 | Bronner et al. |
(Continued)

FOREIGN PATENT DOCUMENTS

| CA | 2138842 A1 | 6/1996 |
| CA | 2366676 A1 | 9/2000 |
(Continued)

OTHER PUBLICATIONS

Notice of Allowance issued in U.S. Appl. No. 11/853,701, dated Mar. 14, 2013 [Cited in related U.S. Appl. No. 14/532,635].
(Continued)

*Primary Examiner* — David W Bates
(74) *Attorney, Agent, or Firm* — BakerHostetler

(57) ABSTRACT

An apparatus and method for penetrating bone marrow is provided. The apparatus may include a housing such as a handheld body, a penetrator assembly, a connector that releasably attaches the penetrator assembly to a drill shaft, a gear mechanism, a motor and a power supply and associated circuitry operable to power the motor. The penetrator assembly may include a removable inner trocar and an outer penetrator or needle. It may also include a grooved trocar that allows bone chips to be expelled as the apparatus is inserted into bone marrow. Various connectors are provided to attach the penetrator assembly to the drill shaft.

16 Claims, 10 Drawing Sheets

Related U.S. Application Data

No. 14/532,635, filed on Nov. 4, 2014, now Pat. No. 10,456,149, which is a continuation of application No. 11/253,467, filed on Oct. 19, 2005, now Pat. No. 8,876,826, which is a division of application No. 10/449,476, filed on May 30, 2003, now Pat. No. 7,699,850.

(60) Provisional application No. 60/384,756, filed on May 31, 2002.

(51) Int. Cl.
| | | |
|---|---|---|
| *A61B 10/02* | (2006.01) | |
| *A61B 17/32* | (2006.01) | |
| *A61B 17/3205* | (2006.01) | |
| *A61M 5/158* | (2006.01) | |
| *A61B 17/00* | (2006.01) | |
| *A61B 90/70* | (2016.01) | |
| *A61B 90/11* | (2016.01) | |
| *A61B 50/33* | (2016.01) | |
| *A61B 50/30* | (2016.01) | |
| *A61B 90/00* | (2016.01) | |
| *A61M 1/00* | (2006.01) | |

(52) U.S. Cl.
CPC ...... *A61B 17/1613* (2013.01); *A61B 17/1617* (2013.01); *A61B 17/1622* (2013.01); *A61B 17/32002* (2013.01); *A61B 17/32053* (2013.01); *A61B 17/3423* (2013.01); *A61B 17/3472* (2013.01); *A61B 17/3476* (2013.01); *A61B 17/3496* (2013.01); *A61M 5/158* (2013.01); *A61B 17/1637* (2013.01); *A61B 50/33* (2016.02); *A61B 90/11* (2016.02); *A61B 90/70* (2016.02); *A61B 2010/0208* (2013.01); *A61B 2010/0258* (2013.01); *A61B 2017/0046* (2013.01); *A61B 2017/00398* (2013.01); *A61B 2017/00734* (2013.01); *A61B 2017/320024* (2013.01); *A61B 2017/3405* (2013.01); *A61B 2050/3008* (2016.02); *A61B 2090/034* (2016.02); *A61B 2090/0813* (2016.02); *A61B 2217/005* (2013.01); *A61M 1/84* (2021.05); *A61M 2005/1581* (2013.01); *A61M 2005/1585* (2013.01); *A61M 2210/02* (2013.01)

(56) References Cited

U.S. PATENT DOCUMENTS

| | | |
|---|---|---|
| 1,686,482 A | 10/1928 | Windle |
| 1,954,620 A | 4/1934 | Connell |
| 2,080,202 A | 5/1937 | Drake |
| 2,130,845 A | 9/1938 | Von Issendorff |
| 2,138,842 A | 12/1938 | Drew |
| 2,219,605 A * | 10/1940 | Turkel ............. A61B 10/025 600/566 |
| 2,261,958 A | 11/1941 | Burri |
| 2,317,648 A | 4/1943 | Siqveland et al. |
| 2,318,648 A | 5/1943 | Penfold et al. |
| 2,419,045 A | 4/1947 | Whittaker et al. |
| 2,426,535 A | 8/1947 | Turkel |
| 2,525,588 A | 10/1950 | Cameron et al. |
| 2,525,839 A | 10/1950 | Sparklin |
| 2,590,516 A | 3/1952 | Von Breymann |
| 2,660,635 A | 11/1953 | Wood |
| 2,714,026 A | 7/1955 | Schultz |
| RE24,056 E | 8/1955 | Johansen |
| 2,766,907 A | 10/1956 | Wallace, Jr. |
| 2,773,501 A | 12/1956 | Young et al. |
| 2,817,648 A | 12/1957 | Gould et al. |
| 2,860,635 A | 11/1958 | Wilburn et al. |
| 2,876,369 A | 3/1959 | Doerner |
| 3,022,596 A | 2/1962 | Cannon |
| 3,104,448 A | 9/1963 | Morrow et al. |
| 3,120,845 A | 2/1964 | Horner et al. |
| 3,173,417 A | 3/1965 | Horner et al. |
| 3,175,554 A | 3/1965 | Stewart et al. |
| 3,269,046 A | 8/1966 | Schaefer |
| 3,413,498 A | 11/1968 | Bowen et al. |
| 3,507,276 A | 4/1970 | Burgess et al. |
| 3,519,858 A | 7/1970 | Morganson |
| 3,529,580 A | 9/1970 | Stevens et al. |
| 3,536,943 A | 10/1970 | Bowen et al. |
| 3,543,966 A | 12/1970 | Ryan et al. |
| 3,598,108 A | 8/1971 | Jamshidi et al. |
| 3,664,163 A | 5/1972 | Foote |
| 3,671,699 A | 6/1972 | Matthews |
| 3,697,223 A | 10/1972 | Kovalcik et al. |
| 3,713,417 A | 1/1973 | Shugart et al. |
| 3,734,207 A | 5/1973 | Fishbein |
| 3,750,667 A | 8/1973 | Pshenichny et al. |
| 3,802,555 A | 4/1974 | Grasty et al. |
| 3,815,605 A | 6/1974 | Schmidt et al. |
| 3,835,860 A | 9/1974 | Garretson |
| 3,843,143 A | 10/1974 | Laxson |
| 3,844,291 A | 10/1974 | Moen |
| 3,850,158 A | 11/1974 | Elias et al. |
| 3,893,445 A * | 7/1975 | Hofsess ............. A61B 10/025 600/567 |
| 3,893,455 A | 7/1975 | McNally |
| 3,935,909 A | 2/1976 | Mabuchi et al. |
| 3,976,066 A | 8/1976 | McCartney |
| 3,981,398 A | 9/1976 | Boshoff |
| 3,991,765 A | 11/1976 | Cohen |
| 3,999,110 A | 12/1976 | Ramstrom et al. |
| 4,021,920 A | 5/1977 | Kirschner et al. |
| 4,040,462 A | 8/1977 | Hattan |
| 4,046,254 A | 9/1977 | Kramer |
| 4,099,518 A | 7/1978 | Baylis et al. |
| 4,124,026 A | 11/1978 | Berner et al. |
| 4,142,517 A * | 3/1979 | Contreras Guerrero de Stavropoulos ....... A61B 10/025 600/567 |
| 4,154,026 A | 5/1979 | Palthe |
| 4,157,714 A | 6/1979 | Foltz et al. |
| 4,170,993 A | 10/1979 | Alvarez |
| 4,185,619 A | 1/1980 | Reiss |
| 4,189,266 A | 2/1980 | Koslow |
| 4,194,505 A | 3/1980 | Schmitz |
| 4,200,111 A | 4/1980 | Harris |
| 4,213,462 A | 7/1980 | Sato |
| 4,258,722 A | 3/1981 | Sessions et al. |
| 4,262,676 A | 4/1981 | Jamshidi |
| 4,266,555 A | 5/1981 | Jamshidi |
| 4,269,192 A | 5/1981 | Matsuo |
| 4,299,230 A | 11/1981 | Kubota |
| 4,306,570 A | 12/1981 | Matthews |
| 4,316,463 A | 2/1982 | Schmitz et al. |
| 4,330,093 A | 5/1982 | Chapman, Jr. |
| 4,333,459 A | 6/1982 | Becker |
| 4,334,529 A | 6/1982 | Wirth |
| 4,356,826 A | 11/1982 | Kubota |
| 4,359,052 A | 11/1982 | Staub |
| 4,373,518 A | 2/1983 | Kaiser et al. |
| 4,378,053 A | 3/1983 | Simpson |
| 4,381,777 A | 5/1983 | Garnier |
| 4,393,872 A | 7/1983 | Reznik et al. |
| 4,399,723 A | 8/1983 | Marleau |
| 4,413,760 A | 11/1983 | Paton |
| 4,416,503 A | 11/1983 | Hayes |
| 4,420,085 A | 12/1983 | Wilson et al. |
| 4,441,563 A | 4/1984 | Walton, II |
| 4,461,305 A | 7/1984 | Cibley |
| 4,469,109 A | 9/1984 | Mehl |
| 4,484,577 A | 11/1984 | Sackner et al. |
| 4,487,209 A | 12/1984 | Mehl |
| 4,504,267 A | 3/1985 | Parmelee et al. |
| 4,522,302 A | 6/1985 | Paikoff |
| 4,543,966 A | 10/1985 | Islam et al. |
| 4,553,539 A | 11/1985 | Morris |
| 4,578,064 A | 3/1986 | Sarnoff et al. |

(56) References Cited

U.S. PATENT DOCUMENTS

| | | |
|---|---|---|
| 4,595,322 A | 6/1986 | Clement |
| 4,605,011 A | 8/1986 | Naslund |
| 4,620,539 A | 11/1986 | Andrews et al. |
| 4,623,335 A | 11/1986 | Jackson |
| 4,630,616 A | 12/1986 | Tretinyak |
| 4,645,492 A | 2/1987 | Weeks |
| 4,646,731 A | 3/1987 | Brower |
| 4,654,030 A | 3/1987 | Moll et al. |
| 4,654,492 A | 3/1987 | Koerner et al. |
| 4,655,226 A | 4/1987 | Lee |
| 4,659,329 A | 4/1987 | Annis |
| 4,670,008 A | 6/1987 | Von Albertini |
| 4,691,929 A | 9/1987 | Neumaier et al. |
| 4,692,073 A | 9/1987 | Martindell |
| 4,696,308 A | 9/1987 | Meller et al. |
| 4,702,261 A | 10/1987 | Cornell et al. |
| 4,711,636 A | 12/1987 | Bierman |
| 4,713,061 A | 12/1987 | Tarello et al. |
| 4,716,901 A | 1/1988 | Jackson et al. |
| 4,720,881 A | 1/1988 | Meyers |
| 4,723,945 A | 2/1988 | Theiling |
| 4,728,876 A | 3/1988 | Mongeon et al. |
| 4,736,850 A | 4/1988 | Bowman et al. |
| 4,753,345 A | 6/1988 | Goodsir et al. |
| 4,758,225 A | 7/1988 | Cox et al. |
| 4,762,118 A | 8/1988 | Lia et al. |
| 4,772,261 A | 9/1988 | Von Hoff et al. |
| 4,787,893 A | 11/1988 | Villette |
| 4,793,363 A | 12/1988 | Ausherman et al. |
| 4,801,293 A | 1/1989 | Jackson |
| 4,810,248 A | 3/1989 | Masters et al. |
| 4,812,008 A | 3/1989 | Tokumaru et al. |
| 4,838,282 A | 6/1989 | Strasser et al. |
| 4,838,877 A | 6/1989 | Massau |
| 4,844,259 A | 7/1989 | Glowczewskie et al. |
| 4,867,158 A | 9/1989 | Sugg |
| 4,874,181 A | 10/1989 | Hsu |
| 4,883,470 A | 11/1989 | Haindl |
| 4,919,146 A | 4/1990 | Rhinehart et al. |
| 4,919,653 A | 4/1990 | Martinez et al. |
| 4,921,013 A | 5/1990 | Spalink et al. |
| 4,922,602 A | 5/1990 | Mehl |
| 4,935,010 A | 6/1990 | Cox et al. |
| 4,940,459 A | 7/1990 | Noce |
| 4,944,677 A | 7/1990 | Alexandre |
| 4,969,870 A | 11/1990 | Kramer et al. |
| 4,976,269 A | 12/1990 | Mehl |
| 4,986,279 A | 1/1991 | ONeill |
| 5,002,546 A | 3/1991 | Romano |
| 5,012,605 A | 5/1991 | Nishioka |
| 5,025,797 A | 6/1991 | Baran |
| 5,036,860 A | 8/1991 | Leigh et al. |
| 5,040,542 A | 8/1991 | Gray |
| 5,057,085 A | 10/1991 | Kopans |
| 5,064,426 A | 11/1991 | Huebsch |
| 5,074,311 A | 12/1991 | Hasson |
| 5,075,994 A | 12/1991 | Nishioka |
| 5,104,382 A | 4/1992 | Brinkerhoff et al. |
| 5,116,324 A | 5/1992 | Brierley et al. |
| 5,120,312 A | 6/1992 | Wigness et al. |
| 5,122,114 A | 6/1992 | Miller et al. |
| 5,133,359 A | 7/1992 | Kedem |
| 5,137,500 A | 8/1992 | Lhotak |
| 5,137,518 A | 8/1992 | Mersch |
| 5,139,500 A | 8/1992 | Schwartz |
| RE34,056 E | 9/1992 | Lindgren et al. |
| 5,145,369 A | 9/1992 | Lustig et al. |
| 5,148,813 A | 9/1992 | Bucalo |
| 5,156,399 A | 10/1992 | Gauer |
| 5,159,163 A | 10/1992 | Bahjat et al. |
| 5,172,700 A | 12/1992 | Bencini et al. |
| 5,172,701 A | 12/1992 | Leigh |
| 5,172,702 A | 12/1992 | Leigh et al. |
| 5,176,415 A | 1/1993 | Choksi |
| 5,176,643 A | 1/1993 | Kramer et al. |
| 5,183,054 A | 2/1993 | Burkholder et al. |
| 5,184,611 A | 2/1993 | Turnbull |
| 5,187,422 A | 2/1993 | Izenbaard et al. |
| 5,195,985 A | 3/1993 | Hall |
| 5,203,056 A | 4/1993 | Funk et al. |
| 5,204,670 A | 4/1993 | Stinton |
| 5,207,303 A | 5/1993 | Oswalt et al. |
| 5,207,697 A * | 5/1993 | Carusillo ........... A61B 17/1626 320/115 |
| 5,209,721 A | 5/1993 | Wilk |
| 5,210,376 A | 5/1993 | Caviar |
| 5,217,478 A | 6/1993 | Rexroth |
| D338,270 S | 8/1993 | Stephens et al. |
| 5,244,619 A | 9/1993 | Burnham |
| 5,249,583 A | 10/1993 | Mallaby |
| 5,257,632 A | 11/1993 | Turkel et al. |
| 5,257,972 A | 11/1993 | Gurmarnik |
| 5,261,877 A | 11/1993 | Fine et al. |
| 5,261,891 A | 11/1993 | Brinkerhoff et al. |
| 5,269,785 A | 12/1993 | Bonutti |
| 5,271,380 A | 12/1993 | Riek et al. |
| 5,271,414 A | 12/1993 | Partika et al. |
| 5,271,744 A | 12/1993 | Kramer et al. |
| 5,279,306 A | 1/1994 | Mehl |
| 5,300,070 A | 4/1994 | Gentelia et al. |
| 5,312,351 A | 5/1994 | Gerrone |
| 5,312,361 A | 5/1994 | Zadini et al. |
| 5,312,364 A | 5/1994 | Jacobs |
| 5,312,408 A | 5/1994 | Brown |
| 5,313,733 A | 5/1994 | Meade |
| 5,315,737 A | 5/1994 | Ouimet |
| 5,318,543 A | 6/1994 | Ross et al. |
| 5,318,589 A | 6/1994 | Lichtman |
| 5,320,110 A | 6/1994 | Wang |
| 5,324,300 A | 6/1994 | Elias et al. |
| 5,330,480 A | 7/1994 | Meloul et al. |
| 5,331,972 A | 7/1994 | Wadhwani et al. |
| 5,332,398 A | 7/1994 | Miller et al. |
| 5,333,790 A | 8/1994 | Christopher |
| 5,334,169 A | 8/1994 | Brown et al. |
| 5,334,204 A | 8/1994 | Clewett et al. |
| 5,339,831 A | 8/1994 | Thompson |
| 5,341,316 A | 8/1994 | Nishigaki |
| 5,341,816 A | 8/1994 | Allen |
| 5,341,823 A | 8/1994 | Manosalva et al. |
| 5,344,420 A | 9/1994 | Hilal et al. |
| 5,348,022 A | 9/1994 | Leigh et al. |
| 5,354,287 A | 10/1994 | Wacks |
| 5,356,006 A | 10/1994 | Alpern et al. |
| 5,357,974 A | 10/1994 | Baldridge |
| 5,357,979 A | 10/1994 | Imran |
| 5,361,853 A * | 11/1994 | Takamura ............... B25B 21/00 173/117 |
| 5,366,445 A | 11/1994 | Haber et al. |
| 5,368,046 A | 11/1994 | Scarfone et al. |
| 5,372,583 A | 12/1994 | Roberts et al. |
| 5,383,859 A | 1/1995 | Sewell, Jr. |
| 5,385,151 A | 1/1995 | Scarfone et al. |
| 5,385,553 A | 1/1995 | Hart et al. |
| 5,389,553 A | 2/1995 | Grubisich et al. |
| 5,400,798 A | 3/1995 | Baran |
| 5,405,348 A | 4/1995 | Anspach, Jr. et al. |
| 5,405,362 A | 4/1995 | Kramer et al. |
| 5,407,243 A | 4/1995 | Riemann |
| 5,421,821 A | 6/1995 | Janicki et al. |
| 5,423,796 A | 6/1995 | Shikhman et al. |
| 5,423,824 A | 6/1995 | Akerfeldt et al. |
| 5,431,151 A | 7/1995 | Riek et al. |
| 5,431,655 A | 7/1995 | Melker et al. |
| 5,432,459 A | 7/1995 | Thompson et al. |
| 5,436,566 A | 7/1995 | Thompson et al. |
| 5,437,119 A | 8/1995 | Womack |
| 5,449,370 A | 9/1995 | Vaitekunas |
| 5,451,210 A | 9/1995 | Kramer et al. |
| 5,454,791 A | 10/1995 | Tovey et al. |
| 5,462,062 A | 10/1995 | Rubinstein et al. |
| 5,476,102 A | 12/1995 | Como et al. |
| 5,480,388 A | 1/1996 | Zadini et al. |
| 5,484,442 A | 1/1996 | Melker et al. |

(56) References Cited

U.S. PATENT DOCUMENTS

| | | |
|---|---|---|
| 5,497,787 A | 3/1996 | Nemesdy et al. |
| 5,499,997 A | 3/1996 | Sharpe et al. |
| 5,505,737 A | 4/1996 | Gosselin et al. |
| D369,858 S | 5/1996 | Baker et al. |
| 5,514,097 A | 5/1996 | Knauer |
| 5,526,820 A | 6/1996 | Khoury |
| 5,526,821 A | 6/1996 | Jamshidi |
| 5,526,822 A | 6/1996 | Burbank et al. |
| 5,527,290 A | 6/1996 | Zadini et al. |
| 5,529,580 A | 6/1996 | Kusunoki et al. |
| 5,533,843 A | 7/1996 | Chung |
| 5,549,565 A | 8/1996 | Ryan et al. |
| 5,554,154 A | 9/1996 | Rosenberg |
| 5,556,399 A | 9/1996 | Huebner |
| 5,558,737 A | 9/1996 | Brown et al. |
| 5,571,133 A | 11/1996 | Yoon |
| 5,586,847 A | 12/1996 | Mattern, Jr. et al. |
| 5,591,119 A | 1/1997 | Adair |
| 5,591,188 A | 1/1997 | Waisman |
| 5,595,186 A | 1/1997 | Rubinstein et al. |
| 5,599,347 A | 2/1997 | Hart et al. |
| 5,599,348 A | 2/1997 | Gentelia et al. |
| 5,601,559 A | 2/1997 | Melker et al. |
| 5,624,214 A | 4/1997 | Carroll |
| 5,632,747 A | 5/1997 | Scarborough et al. |
| 5,649,547 A | 7/1997 | Ritchart et al. |
| 5,651,419 A | 7/1997 | Holzer et al. |
| 5,672,155 A | 9/1997 | Riley et al. |
| 5,685,820 A | 11/1997 | Riek et al. |
| 5,687,802 A | 11/1997 | Spooner et al. |
| 5,693,031 A | 12/1997 | Ryan et al. |
| 5,709,275 A | 1/1998 | Anton |
| 5,712,543 A | 1/1998 | Sjostrom |
| 5,713,149 A | 2/1998 | Cady et al. |
| 5,713,368 A | 2/1998 | Leigh |
| 5,724,873 A | 3/1998 | Hillinger |
| 5,733,262 A | 3/1998 | Paul |
| 5,738,177 A | 4/1998 | Schell et al. |
| 5,752,923 A | 5/1998 | Terwilliger |
| 5,762,498 A | 6/1998 | Arnaldo |
| 5,762,639 A * | 6/1998 | Gibbs ............... A61B 17/3472 604/264 |
| 5,766,221 A | 6/1998 | Benderev et al. |
| 5,769,086 A | 6/1998 | Ritchart et al. |
| 5,779,708 A | 7/1998 | Wu |
| 5,800,389 A | 9/1998 | Burney et al. |
| 5,801,454 A | 9/1998 | Leininger |
| 5,807,275 A | 9/1998 | Jamshidi |
| 5,807,277 A | 9/1998 | Swaim |
| 5,809,653 A | 9/1998 | Everts et al. |
| 5,810,826 A | 9/1998 | Akerfeldt et al. |
| 5,817,052 A | 10/1998 | Johnson et al. |
| 5,823,970 A | 10/1998 | Terwilliger |
| D403,405 S | 12/1998 | Terwilliger |
| D404,458 S | 1/1999 | Pruitt |
| 5,858,005 A | 1/1999 | Kriesel |
| 5,865,711 A | 2/1999 | Chen |
| 5,868,711 A | 2/1999 | Kramer et al. |
| 5,868,750 A | 2/1999 | Schultz |
| 5,873,499 A | 2/1999 | Leschinsky et al. |
| 5,873,510 A | 2/1999 | Hirai et al. |
| 5,873,580 A * | 2/1999 | Swenson, Sr. ........ B23B 31/202 279/46.3 |
| 5,885,226 A | 3/1999 | Rubinstein et al. |
| 5,891,085 A | 4/1999 | Lilley et al. |
| 5,893,851 A | 4/1999 | Umber et al. |
| 5,906,797 A | 5/1999 | Orihara et al. |
| 5,910,121 A | 6/1999 | Avaltroni et al. |
| 5,911,701 A | 6/1999 | Miller et al. |
| 5,911,708 A | 6/1999 | Teirstein |
| 5,916,229 A | 6/1999 | Evans |
| 5,919,172 A | 7/1999 | Golba, Jr. |
| 5,921,562 A | 7/1999 | Robison |
| 5,921,987 A | 7/1999 | Stone |
| 5,924,864 A | 7/1999 | Loge et al. |
| 5,926,989 A | 7/1999 | Oliver, Sr. |
| 5,927,976 A | 7/1999 | Wu |
| 5,928,164 A | 7/1999 | Burbank et al. |
| 5,928,238 A | 7/1999 | Scarborough et al. |
| 5,928,241 A | 7/1999 | Menut et al. |
| 5,938,636 A | 8/1999 | Kramer et al. |
| 5,941,706 A | 8/1999 | Ura |
| 5,941,841 A | 8/1999 | Mutch et al. |
| 5,941,851 A | 8/1999 | Coffey et al. |
| 5,945,896 A | 8/1999 | Miyamoto |
| 5,947,989 A | 9/1999 | Shikhman et al. |
| 5,951,026 A | 9/1999 | Harman, Jr. et al. |
| 5,954,671 A | 9/1999 | O'Neill |
| 5,954,701 A | 9/1999 | Matalon |
| 5,960,575 A | 10/1999 | Chiovitt et al. |
| 5,960,797 A | 10/1999 | Kramer et al. |
| 5,980,469 A | 11/1999 | Burbank et al. |
| 5,980,545 A | 11/1999 | Pacala et al. |
| 5,984,020 A | 11/1999 | Meyer et al. |
| 5,984,919 A | 11/1999 | Hilal et al. |
| 5,989,257 A | 11/1999 | Tidwell et al. |
| 5,993,417 A | 11/1999 | Yerfino et al. |
| 5,993,454 A | 11/1999 | Longo |
| 6,007,481 A | 12/1999 | Riek et al. |
| 6,007,496 A | 12/1999 | Brannon |
| 6,015,391 A | 1/2000 | Rishton et al. |
| 6,017,348 A | 1/2000 | Hart et al. |
| 6,018,094 A | 1/2000 | Fox |
| 6,018,230 A | 1/2000 | Casey |
| 6,022,324 A | 2/2000 | Skinner |
| 6,025,683 A | 2/2000 | Philipp |
| 6,027,458 A | 2/2000 | Janssens |
| 6,033,369 A | 3/2000 | Goldenberg |
| 6,033,408 A | 3/2000 | Gage et al. |
| 6,033,411 A | 3/2000 | Preissman |
| 6,042,585 A | 3/2000 | Norman |
| 6,049,725 A | 4/2000 | Emmert et al. |
| 6,050,754 A | 4/2000 | Thomas |
| 6,059,806 A | 5/2000 | Hoegerle |
| 6,063,037 A | 5/2000 | Mittermeier et al. |
| 6,066,938 A | 5/2000 | Hyodo et al. |
| 6,071,284 A | 6/2000 | Fox |
| 6,080,115 A | 6/2000 | Rubinstein |
| 6,083,176 A | 7/2000 | Terwilliger |
| 6,086,543 A | 7/2000 | Anderson et al. |
| 6,086,544 A | 7/2000 | Hibner et al. |
| 6,092,355 A | 7/2000 | Ishmael |
| 6,096,042 A | 8/2000 | Herbert |
| 6,098,042 A | 8/2000 | Huynh |
| 6,102,887 A | 8/2000 | Altman |
| 6,102,915 A | 8/2000 | Bresler et al. |
| 6,106,484 A | 8/2000 | Terwilliger |
| 6,110,128 A | 8/2000 | Andelin et al. |
| 6,110,129 A | 8/2000 | Terwilliger |
| 6,110,174 A | 8/2000 | Nichter |
| 6,120,462 A | 9/2000 | Hibner et al. |
| 6,126,670 A | 10/2000 | Walker et al. |
| 6,129,106 A | 10/2000 | Kornelson et al. |
| 6,135,769 A | 10/2000 | Kwan |
| 6,152,918 A | 11/2000 | Padilla et al. |
| 6,154,995 A | 12/2000 | Lenoir et al. |
| 6,159,163 A | 12/2000 | Strauss et al. |
| 6,162,203 A | 12/2000 | Haaga |
| 6,171,276 B1 | 1/2001 | Lippe et al. |
| 6,183,442 B1 | 2/2001 | Athanasiou et al. |
| 6,187,768 B1 | 2/2001 | Welle et al. |
| 6,210,376 B1 | 4/2001 | Grayson |
| 6,217,561 B1 | 4/2001 | Gibbs |
| 6,221,029 B1 | 4/2001 | Mathis et al. |
| 6,228,049 B1 | 5/2001 | Schroeder et al. |
| 6,228,088 B1 | 5/2001 | Miller et al. |
| 6,231,996 B1 | 5/2001 | Umeno et al. |
| 6,238,355 B1 | 5/2001 | Daum |
| 6,241,734 B1 | 6/2001 | Scribner et al. |
| 6,242,009 B1 | 6/2001 | Batarseh et al. |
| 6,247,110 B1 | 6/2001 | Huppenthal et al. |
| 6,247,928 B1 | 6/2001 | Meller et al. |
| 6,248,110 B1 | 6/2001 | Reiley et al. |
| 6,257,351 B1 | 7/2001 | Ark et al. |

(56) References Cited

U.S. PATENT DOCUMENTS

| | | |
|---|---|---|
| 6,261,272 B1 | 7/2001 | Gross et al. |
| 6,267,763 B1 | 7/2001 | Castro |
| 6,270,087 B1 | 8/2001 | Mickel et al. |
| 6,272,007 B1 | 8/2001 | Kitlas et al. |
| 6,273,715 B1 | 8/2001 | Meller et al. |
| 6,273,862 B1 | 8/2001 | Privitera et al. |
| 6,283,925 B1 | 9/2001 | Terwilliger |
| 6,283,970 B1 | 9/2001 | Lubinus |
| 6,287,114 B1 | 9/2001 | Meller et al. |
| 6,302,409 B1 | 10/2001 | Gutsche |
| 6,302,852 B1 | 10/2001 | Fleming, III et al. |
| 6,308,540 B1 | 10/2001 | Lee |
| 6,309,258 B1 | 10/2001 | Measley |
| 6,309,358 B1 | 10/2001 | Okubo |
| 6,312,394 B1 | 11/2001 | Fleming, III |
| 6,315,737 B1 | 11/2001 | Skinner |
| 6,321,855 B1 | 11/2001 | Barnes |
| 6,325,806 B1 | 12/2001 | Fox |
| 6,328,701 B1 | 12/2001 | Terwilliger |
| 6,328,744 B1 | 12/2001 | Harari et al. |
| 6,349,496 B1 | 2/2002 | Neely |
| 6,358,252 B1 | 3/2002 | Shapira |
| 6,382,212 B1 | 5/2002 | Borchard |
| 6,402,701 B1 | 6/2002 | Kaplan et al. |
| 6,416,484 B1 | 7/2002 | Miller et al. |
| 6,419,490 B1 | 7/2002 | Kitchings Weathers, Jr. |
| 6,425,388 B1 | 7/2002 | Korinchock |
| 6,425,888 B1 | 7/2002 | Embleton et al. |
| 6,428,487 B1 | 8/2002 | Burdorff et al. |
| 6,443,910 B1 | 9/2002 | Krueger et al. |
| 6,446,734 B1 | 9/2002 | Williams et al. |
| 6,450,973 B1 | 9/2002 | Murphy |
| 6,451,023 B1 | 9/2002 | Salazar et al. |
| 6,458,117 B1 | 10/2002 | Pollins, Sr. |
| 6,468,248 B1 | 10/2002 | Gibbs |
| 6,478,751 B1 | 11/2002 | Krueger et al. |
| 6,488,636 B2 | 12/2002 | Bryan et al. |
| 6,494,590 B1 | 12/2002 | Paganini et al. |
| 6,520,971 B1 | 2/2003 | Perry et al. |
| 6,523,698 B1 | 2/2003 | Dennehey et al. |
| 6,527,736 B1 | 3/2003 | Attinger et al. |
| 6,527,778 B2 | 3/2003 | Athanasiou et al. |
| 6,537,242 B1 | 3/2003 | Palmer |
| 6,540,694 B1 | 4/2003 | Van Bladel et al. |
| 6,540,697 B2 | 4/2003 | Chen |
| 6,547,451 B1 | 4/2003 | Nishikawa et al. |
| 6,547,511 B1 | 4/2003 | Adams |
| 6,547,561 B2 | 4/2003 | Meller et al. |
| 6,547,755 B1 | 4/2003 | Lippe et al. |
| 6,549,511 B1 | 4/2003 | Prikryl |
| 6,550,786 B2 | 4/2003 | Gifford et al. |
| 6,554,779 B2 | 4/2003 | Viola et al. |
| 6,555,212 B2 | 4/2003 | Boiocchi et al. |
| 6,572,563 B2 | 6/2003 | Ouchi |
| 6,575,745 B2 | 6/2003 | Meller et al. |
| 6,575,919 B1 | 6/2003 | Reiley et al. |
| 6,582,399 B1 | 6/2003 | Smith et al. |
| 6,585,622 B1 | 7/2003 | Shum et al. |
| 6,595,362 B2 | 7/2003 | Penney et al. |
| 6,595,911 B2 | 7/2003 | LoVuolo |
| 6,595,979 B1 | 7/2003 | Epstein et al. |
| 6,613,054 B2 | 9/2003 | Scribner et al. |
| 6,616,632 B2 | 9/2003 | Sharp et al. |
| 6,620,111 B2 | 9/2003 | Stephens et al. |
| 6,622,731 B2 | 9/2003 | Daniel et al. |
| 6,626,173 B2 | 9/2003 | Genova et al. |
| 6,626,848 B2 | 9/2003 | Neuenfeldt |
| 6,626,887 B2 | 9/2003 | Wu |
| 6,638,235 B2 | 10/2003 | Miller et al. |
| 6,641,395 B2 | 11/2003 | Kumar et al. |
| 6,656,133 B2 | 12/2003 | Voegele et al. |
| 6,689,072 B2 | 2/2004 | Kaplan et al. |
| 6,690,308 B2 | 2/2004 | Hayami |
| 6,702,760 B2 | 3/2004 | Krause et al. |
| 6,702,761 B1 | 3/2004 | Damadian et al. |
| 6,706,016 B2 | 3/2004 | Cory et al. |
| 6,716,192 B1 | 4/2004 | Orosz, Jr. |
| 6,716,215 B1 | 4/2004 | David et al. |
| 6,716,216 B1 | 4/2004 | Boucher et al. |
| 6,726,649 B2 | 4/2004 | Swenson et al. |
| 6,730,043 B2 | 5/2004 | Krueger et al. |
| 6,730,044 B2 | 5/2004 | Stephens et al. |
| 6,749,576 B2 | 6/2004 | Bauer |
| 6,752,768 B2 | 6/2004 | Burdorff et al. |
| 6,752,816 B2 | 6/2004 | Culp et al. |
| 6,758,824 B1 | 7/2004 | Miller et al. |
| 6,761,726 B1 | 7/2004 | Findlay et al. |
| 6,770,070 B1 | 8/2004 | Balbierz |
| 6,783,532 B2 | 8/2004 | Steiner et al. |
| 6,796,957 B2 | 9/2004 | Carpenter et al. |
| 6,839,789 B2 | 1/2005 | Kraemer et al. |
| 6,846,314 B2 | 1/2005 | Shapira |
| 6,849,051 B2 | 2/2005 | Sramek et al. |
| 6,855,148 B2 | 2/2005 | Foley et al. |
| 6,860,860 B2 | 3/2005 | Viola |
| 6,871,759 B2 | 3/2005 | Rake et al. |
| 6,872,187 B1 | 3/2005 | Stark et al. |
| 6,875,163 B2 | 4/2005 | Cercone et al. |
| 6,875,183 B2 | 4/2005 | Cervi |
| 6,875,219 B2 | 4/2005 | Arramon et al. |
| 6,884,245 B2 | 4/2005 | Spranza, III |
| 6,887,209 B2 | 5/2005 | Kadziauskas et al. |
| 6,890,308 B2 | 5/2005 | Islam |
| 6,896,141 B2 | 5/2005 | McMichael et al. |
| 6,902,559 B2 | 6/2005 | Taufig |
| 6,905,466 B2 | 6/2005 | Salgo et al. |
| 6,905,486 B2 | 6/2005 | Gibbs |
| 6,916,292 B2 | 7/2005 | Morawski et al. |
| 6,930,461 B2 | 8/2005 | Rutkowski |
| 6,942,669 B2 | 9/2005 | Kurc |
| 6,947,669 B2 | 9/2005 | Wu et al. |
| 6,969,373 B2 | 11/2005 | Schwartz et al. |
| 7,001,342 B2 | 2/2006 | Faciszewski |
| 7,008,381 B2 | 3/2006 | Janssens |
| 7,008,383 B1 | 3/2006 | Damadian et al. |
| 7,008,394 B2 | 3/2006 | Geise et al. |
| 7,014,614 B2 | 3/2006 | Casula |
| 7,018,343 B2 | 3/2006 | Plishka |
| 7,025,732 B2 | 4/2006 | Thompson et al. |
| 7,033,324 B2 | 4/2006 | Giusti et al. |
| 7,063,672 B2 | 6/2006 | Schramm |
| 7,063,703 B2 | 6/2006 | Reo |
| 7,081,123 B2 | 7/2006 | Merboth et al. |
| 7,108,696 B2 | 9/2006 | Daniel et al. |
| 7,134,815 B2 | 11/2006 | Steer |
| 7,137,985 B2 | 11/2006 | Jahng |
| 7,169,127 B2 | 1/2007 | Epstein et al. |
| 7,182,752 B2 | 2/2007 | Stubbs et al. |
| 7,186,257 B2 | 3/2007 | Kim |
| 7,207,949 B2 | 4/2007 | Miles et al. |
| 7,212,011 B2 | 5/2007 | Shimizu et al. |
| 7,226,450 B2 | 6/2007 | Athanasiou et al. |
| 7,229,401 B2 | 6/2007 | Kindlein |
| 7,278,972 B2 | 10/2007 | Lamoureux et al. |
| 7,285,112 B2 | 10/2007 | Stubbs et al. |
| 7,331,462 B2 | 2/2008 | Steppe |
| 7,331,930 B2 | 2/2008 | Faciszewski |
| 7,338,473 B2 | 3/2008 | Campbell et al. |
| 7,413,559 B2 | 8/2008 | Stubbs et al. |
| 7,513,722 B2 | 4/2009 | Greenberg et al. |
| 7,565,935 B1 | 7/2009 | Phillips |
| 7,615,043 B2 | 11/2009 | Zhou |
| 7,670,328 B2 | 3/2010 | Miller |
| 7,699,850 B2 | 4/2010 | Miller |
| 7,736,322 B2 | 6/2010 | Roe et al. |
| 7,798,331 B2 | 9/2010 | Hardin et al. |
| 7,811,260 B2 | 10/2010 | Miller et al. |
| 7,815,642 B2 | 10/2010 | Miller |
| 7,850,620 B2 | 12/2010 | Miller et al. |
| 7,854,724 B2 | 12/2010 | Stearns et al. |
| 7,899,528 B2 | 3/2011 | Miller et al. |
| 7,934,333 B1 | 5/2011 | Tuz |
| 7,951,089 B2 | 5/2011 | Miller |
| 7,988,643 B2 | 8/2011 | Hoffmann et al. |

(56) References Cited

U.S. PATENT DOCUMENTS

| | | |
|---|---|---|
| 8,038,664 B2 | 10/2011 | Miller et al. |
| 8,088,189 B2 | 1/2012 | Matula et al. |
| 8,092,457 B2 | 1/2012 | Oettinger et al. |
| 8,142,365 B2 | 3/2012 | Miller |
| 8,216,189 B2 | 7/2012 | Stubbs et al. |
| 8,217,561 B2 | 7/2012 | Fukuzawa et al. |
| 8,277,411 B2 | 10/2012 | Gellman |
| 8,282,565 B2 | 10/2012 | Mahapatra et al. |
| 8,308,693 B2 | 11/2012 | Miller et al. |
| 8,317,815 B2 | 11/2012 | Mastri et al. |
| 8,419,683 B2 | 4/2013 | Miller et al. |
| 8,480,632 B2 | 7/2013 | Miller et al. |
| 8,506,568 B2 | 8/2013 | Miller |
| 8,641,715 B2 | 2/2014 | Miller |
| 8,656,929 B2 | 2/2014 | Miller et al. |
| 8,668,698 B2 | 3/2014 | Miller et al. |
| 8,684,978 B2 | 4/2014 | Miller et al. |
| 8,690,791 B2 | 4/2014 | Miller |
| 8,715,219 B2 | 5/2014 | Stearns et al. |
| 8,715,287 B2 | 5/2014 | Miller |
| 8,720,097 B2 | 5/2014 | Derman |
| 8,812,101 B2 | 8/2014 | Miller et al. |
| 8,814,807 B2 | 8/2014 | Hulvershorn et al. |
| 8,870,872 B2 | 10/2014 | Miller |
| 8,876,826 B2 | 11/2014 | Miller |
| 8,920,388 B2 | 12/2014 | Slocum et al. |
| 8,926,525 B2 | 1/2015 | Hulvershorn et al. |
| 8,944,069 B2 | 2/2015 | Miller et al. |
| 8,961,451 B2 | 2/2015 | Stearns et al. |
| 8,974,410 B2 | 3/2015 | Miller et al. |
| 8,974,569 B2 | 3/2015 | Matula et al. |
| 8,992,535 B2 | 3/2015 | Miller |
| 8,998,348 B2 | 4/2015 | Frank |
| 8,998,848 B2 | 4/2015 | Miller et al. |
| 9,067,030 B2 | 6/2015 | Stearns et al. |
| 9,072,543 B2 | 7/2015 | Miller et al. |
| 9,078,637 B2 | 7/2015 | Miller |
| 9,095,372 B2 | 8/2015 | Stearns et al. |
| 9,110,104 B2 | 8/2015 | Chung et al. |
| 9,186,172 B2 | 11/2015 | Velez Rivera |
| 9,199,047 B2 | 12/2015 | Stearns et al. |
| 9,295,487 B2 | 3/2016 | Miller et al. |
| 9,314,228 B2 | 4/2016 | Miller |
| 9,314,270 B2 | 4/2016 | Miller |
| 9,439,667 B2 | 9/2016 | Miller |
| 9,451,968 B2 | 9/2016 | Miller et al. |
| 9,504,477 B2 | 11/2016 | Miller et al. |
| 9,545,243 B2 | 1/2017 | Miller et al. |
| 9,662,160 B2 | 5/2017 | Beale et al. |
| 9,717,564 B2 | 8/2017 | Miller et al. |
| 9,717,847 B2 | 8/2017 | Miller et al. |
| 9,826,984 B2 | 11/2017 | McGinley et al. |
| 9,872,703 B2 | 1/2018 | Miller et al. |
| 10,016,217 B2 | 7/2018 | Miller |
| 10,052,111 B2 | 8/2018 | Miller et al. |
| 10,081,414 B2 | 9/2018 | Le Devehat et al. |
| 10,149,686 B2 | 12/2018 | Anderson |
| 10,245,010 B2 | 4/2019 | Miller et al. |
| 10,258,783 B2 | 4/2019 | Miller et al. |
| 10,456,149 B2 | 10/2019 | Miller |
| 10,512,474 B2 | 12/2019 | Miller et al. |
| 10,722,247 B2 | 7/2020 | Browne et al. |
| 10,806,491 B2 | 10/2020 | Miller et al. |
| 10,893,875 B2 | 1/2021 | Miller |
| 11,103,281 B2 | 8/2021 | Miller |
| 11,103,282 B1 | 8/2021 | Miller et al. |
| 2001/0005778 A1 | 6/2001 | Ouchi |
| 2001/0014439 A1* | 8/2001 | Meller .................. A61C 1/081 433/50 |
| 2001/0026051 A1 | 10/2001 | Gifford et al. |
| 2001/0034527 A1 | 10/2001 | Scribner et al. |
| 2001/0047183 A1 | 11/2001 | Privitera et al. |
| 2001/0053888 A1 | 12/2001 | Athanasiou et al. |
| 2002/0018102 A1 | 2/2002 | Nozawa |
| 2002/0029007 A1 | 3/2002 | Bryan et al. |
| 2002/0042581 A1 | 4/2002 | Cervi |
| 2002/0050364 A1 | 5/2002 | Suzuki et al. |
| 2002/0055713 A1 | 5/2002 | Gibbs |
| 2002/0091039 A1 | 7/2002 | Reinbold et al. |
| 2002/0096343 A1 | 7/2002 | Potter et al. |
| 2002/0120212 A1 | 8/2002 | Ritchart et al. |
| 2002/0133148 A1 | 9/2002 | Daniel et al. |
| 2002/0138021 A1 | 9/2002 | Pflueger |
| 2002/0143269 A1 | 10/2002 | Neuenfeldt |
| 2002/0151821 A1 | 10/2002 | Castellacci |
| 2002/0151902 A1 | 10/2002 | Riedel et al. |
| 2002/0158102 A1 | 10/2002 | Patton et al. |
| 2003/0009132 A1 | 1/2003 | Schwartz et al. |
| 2003/0023256 A1 | 1/2003 | Estes et al. |
| 2003/0028146 A1 | 2/2003 | Aves |
| 2003/0032939 A1 | 2/2003 | Gibbs |
| 2003/0036747 A1 | 2/2003 | Ie et al. |
| 2003/0050574 A1 | 3/2003 | Krueger |
| 2003/0078586 A1 | 4/2003 | Shapira |
| 2003/0078589 A1 | 4/2003 | Preissman |
| 2003/0114858 A1 | 6/2003 | Athanasiou et al. |
| 2003/0125639 A1 | 7/2003 | Fisher et al. |
| 2003/0144104 A1* | 7/2003 | Ryberg .................. F16H 1/16 475/149 |
| 2003/0149436 A1 | 8/2003 | McDowell et al. |
| 2003/0153842 A1 | 8/2003 | Lamoureux et al. |
| 2003/0173178 A1 | 9/2003 | Sasaki |
| 2003/0191414 A1 | 10/2003 | Reiley et al. |
| 2003/0195436 A1 | 10/2003 | Van Bladel et al. |
| 2003/0195524 A1 | 10/2003 | Barner |
| 2003/0199787 A1 | 10/2003 | Schwindt |
| 2003/0199879 A1 | 10/2003 | Spranza |
| 2003/0205987 A1 | 11/2003 | Barlev et al. |
| 2003/0212343 A1 | 11/2003 | Plishka |
| 2003/0216667 A1 | 11/2003 | Viola |
| 2003/0225344 A1 | 12/2003 | Miller |
| 2003/0225364 A1 | 12/2003 | Kraft et al. |
| 2003/0225411 A1 | 12/2003 | Miller |
| 2003/0233114 A1 | 12/2003 | Merboth et al. |
| 2004/0010236 A1 | 1/2004 | Morawski et al. |
| 2004/0019297 A1 | 1/2004 | Angel |
| 2004/0019299 A1 | 1/2004 | Ritchart et al. |
| 2004/0031721 A1 | 2/2004 | Mann |
| 2004/0032179 A1 | 2/2004 | Du |
| 2004/0034280 A1 | 2/2004 | Privitera et al. |
| 2004/0049128 A1 | 3/2004 | Miller et al. |
| 2004/0049205 A1 | 3/2004 | Lee et al. |
| 2004/0064136 A1 | 4/2004 | Papineau et al. |
| 2004/0073139 A1 | 4/2004 | Hirsch et al. |
| 2004/0092946 A1 | 5/2004 | Bagga et al. |
| 2004/0127814 A1 | 7/2004 | Negroni |
| 2004/0153003 A1 | 8/2004 | Cicenas et al. |
| 2004/0158172 A1 | 8/2004 | Hancock |
| 2004/0158173 A1 | 8/2004 | Voegele et al. |
| 2004/0162505 A1 | 8/2004 | Kaplan et al. |
| 2004/0167428 A1 | 8/2004 | Quick et al. |
| 2004/0191897 A1 | 9/2004 | Muschler |
| 2004/0210161 A1 | 10/2004 | Burdorff et al. |
| 2004/0210196 A1 | 10/2004 | Bush et al. |
| 2004/0210198 A1 | 10/2004 | Shih |
| 2004/0215102 A1* | 10/2004 | Ikehara ................ A61B 10/025 600/562 |
| 2004/0220497 A1 | 11/2004 | Findlay et al. |
| 2004/0249306 A1 | 12/2004 | Islam |
| 2004/0249389 A1 | 12/2004 | Kim |
| 2004/0259254 A1* | 12/2004 | Honmou ................ A61P 25/00 435/456 |
| 2005/0027210 A1 | 2/2005 | Miller |
| 2005/0033275 A1 | 2/2005 | Hoegerle et al. |
| 2005/0033304 A1 | 2/2005 | O'Heeron |
| 2005/0040060 A1 | 2/2005 | Andersen et al. |
| 2005/0043714 A1 | 2/2005 | Zhou |
| 2005/0075581 A1 | 4/2005 | Schwindt |
| 2005/0085838 A1 | 4/2005 | Thompson et al. |
| 2005/0101880 A1 | 5/2005 | Cicenas et al. |
| 2005/0113716 A1 | 5/2005 | Mueller, Jr. et al. |
| 2005/0116673 A1 | 6/2005 | Carl et al. |
| 2005/0119660 A1 | 6/2005 | Bourlion et al. |
| 2005/0124915 A1 | 6/2005 | Eggers et al. |

(56) References Cited

U.S. PATENT DOCUMENTS

| | | |
|---|---|---|
| 2005/0131345 A1 | 6/2005 | Miller |
| 2005/0148940 A1 | 7/2005 | Miller |
| 2005/0159677 A1 | 7/2005 | Shabaz et al. |
| 2005/0165328 A1 | 7/2005 | Heske et al. |
| 2005/0165403 A1 | 7/2005 | Miller |
| 2005/0165404 A1 | 7/2005 | Miller |
| 2005/0171504 A1 | 8/2005 | Miller |
| 2005/0182394 A1 | 8/2005 | Spero et al. |
| 2005/0200087 A1 | 9/2005 | Vasudeva et al. |
| 2005/0203439 A1 | 9/2005 | Heske et al. |
| 2005/0209530 A1 | 9/2005 | Pflueger |
| 2005/0215921 A1 | 9/2005 | Hibner et al. |
| 2005/0228309 A1 | 10/2005 | Fisher et al. |
| 2005/0236940 A1 | 10/2005 | Rockoff |
| 2005/0261693 A1 | 11/2005 | Miller et al. |
| 2006/0011506 A1 | 1/2006 | Riley |
| 2006/0015066 A1 | 1/2006 | Turieo et al. |
| 2006/0036212 A1 | 2/2006 | Miller |
| 2006/0043685 A1 | 3/2006 | Kozak |
| 2006/0052790 A1 | 3/2006 | Miller |
| 2006/0074345 A1 | 4/2006 | Hibner |
| 2006/0074425 A1 | 4/2006 | Sutterlin et al. |
| 2006/0079774 A1 | 4/2006 | Anderson |
| 2006/0089565 A1 | 4/2006 | Schramm |
| 2006/0111724 A1 | 5/2006 | Yeung Wai Ping |
| 2006/0115066 A1 | 6/2006 | Levien et al. |
| 2006/0122535 A1 | 6/2006 | Daum |
| 2006/0129082 A1 | 6/2006 | Rozga |
| 2006/0144548 A1 | 7/2006 | Beckman et al. |
| 2006/0149163 A1 | 7/2006 | Hibner et al. |
| 2006/0151188 A1 | 7/2006 | Bodine et al. |
| 2006/0167377 A1 | 7/2006 | Ritchart et al. |
| 2006/0167378 A1 | 7/2006 | Miller |
| 2006/0167379 A1 | 7/2006 | Miller |
| 2006/0173480 A1 | 8/2006 | Zhang |
| 2006/0184063 A1 | 8/2006 | Miller |
| 2006/0189940 A1 | 8/2006 | Kirsch |
| 2006/0192350 A1 | 8/2006 | Kleine et al. |
| 2006/0206132 A1 | 9/2006 | Conquergood et al. |
| 2006/0237205 A1 | 10/2006 | Sia et al. |
| 2007/0016100 A1 | 1/2007 | Miller |
| 2007/0024013 A1 | 2/2007 | Hauptmann et al. |
| 2007/0049945 A1 | 3/2007 | Miller |
| 2007/0084742 A1 | 4/2007 | Miller et al. |
| 2007/0120331 A1 | 5/2007 | Manschitz et al. |
| 2007/0149920 A1 | 6/2007 | Michels et al. |
| 2007/0209957 A1 | 9/2007 | Glenn et al. |
| 2007/0213735 A1 | 9/2007 | Saadat et al. |
| 2007/0256914 A1 | 11/2007 | Lohr et al. |
| 2007/0270712 A1 | 11/2007 | Wiksell et al. |
| 2007/0270775 A1 | 11/2007 | Miller et al. |
| 2008/0015467 A1 | 1/2008 | Miller |
| 2008/0015468 A1 | 1/2008 | Miller |
| 2008/0015623 A1 | 1/2008 | Deck |
| 2008/0045857 A1 | 2/2008 | Miller et al. |
| 2008/0045860 A1 | 2/2008 | Miller et al. |
| 2008/0045861 A1 | 2/2008 | Miller et al. |
| 2008/0045965 A1 | 2/2008 | Miller et al. |
| 2008/0072719 A1 | 3/2008 | Kozak |
| 2008/0086160 A1 | 4/2008 | Mastri et al. |
| 2008/0087448 A1 | 4/2008 | Happ |
| 2008/0140014 A1 | 6/2008 | Miller et al. |
| 2008/0177200 A1 | 7/2008 | Ikehara et al. |
| 2008/0215056 A1 | 9/2008 | Miller et al. |
| 2008/0221580 A1 | 9/2008 | Miller et al. |
| 2008/0243163 A1 | 10/2008 | Masseglia et al. |
| 2008/0262383 A1 | 10/2008 | Routhier et al. |
| 2008/0302551 A1 | 12/2008 | Komuro et al. |
| 2009/0069716 A1 | 3/2009 | Freeman et al. |
| 2009/0093677 A1 | 4/2009 | Smith |
| 2009/0131832 A1 | 5/2009 | Sacristan et al. |
| 2009/0194446 A1 | 8/2009 | Miller et al. |
| 2009/0248029 A1 | 10/2009 | Paulos |
| 2009/0311061 A1 | 12/2009 | Santamarina et al. |
| 2010/0137740 A1 | 6/2010 | Miller |
| 2010/0204611 A1 | 8/2010 | Zambelli |
| 2010/0298784 A1 | 11/2010 | Miller |
| 2011/0046477 A1 | 2/2011 | Hulvershorn et al. |
| 2011/0046507 A1 | 2/2011 | Herndon |
| 2011/0071572 A1 | 3/2011 | Sixto et al. |
| 2011/0082387 A1 | 4/2011 | Miller et al. |
| 2011/0098604 A1 | 4/2011 | Miller |
| 2011/0125084 A1 | 5/2011 | Stearns et al. |
| 2011/0184425 A1 | 7/2011 | Cheraux |
| 2011/0186456 A1 | 8/2011 | Bertazzoni et al. |
| 2011/0203821 A1 | 8/2011 | Puzio et al. |
| 2011/0251518 A1 | 10/2011 | Swisher et al. |
| 2011/0288405 A1 | 11/2011 | Razavi et al. |
| 2011/0306841 A1 | 12/2011 | Lozman et al. |
| 2012/0109061 A1 | 5/2012 | Miller et al. |
| 2012/0150101 A1 | 6/2012 | Stearns et al. |
| 2012/0165832 A1 | 6/2012 | Oostman et al. |
| 2012/0283582 A1 | 11/2012 | Mahapatra et al. |
| 2012/0323071 A1 | 12/2012 | Gellman |
| 2012/0330184 A1 | 12/2012 | Mahapatra et al. |
| 2013/0213843 A1 | 8/2013 | Knight et al. |
| 2014/0005657 A1 | 1/2014 | Brannan et al. |
| 2014/0188038 A1 | 7/2014 | Stearns et al. |
| 2014/0231302 A1 | 8/2014 | Goyal |
| 2014/0262408 A1 | 9/2014 | Woodard |
| 2014/0311302 A1 | 10/2014 | Taguchi et al. |
| 2014/0336567 A1 | 11/2014 | Stearns et al. |
| 2014/0343454 A1 | 11/2014 | Miller et al. |
| 2014/0358070 A1 | 12/2014 | Stearns et al. |
| 2015/0025363 A1 | 1/2015 | Hulvershorn et al. |
| 2015/0057530 A1 | 2/2015 | Roggeveen et al. |
| 2015/0112261 A1 | 4/2015 | Bassett et al. |
| 2015/0127006 A1 | 5/2015 | Miller |
| 2015/0129456 A1 | 5/2015 | Miller et al. |
| 2015/0173818 A1 | 6/2015 | Baroud et al. |
| 2015/0202390 A1 | 7/2015 | Stearns et al. |
| 2015/0202391 A1 | 7/2015 | Stearns et al. |
| 2015/0223786 A1 | 8/2015 | Morgan et al. |
| 2015/0230823 A1 | 8/2015 | Morgan et al. |
| 2015/0342635 A1 | 12/2015 | Tsamir et al. |
| 2015/0366569 A1 | 12/2015 | Miller |
| 2016/0081732 A1 | 3/2016 | Baroud |
| 2017/0036328 A1 | 2/2017 | Chen |
| 2017/0266790 A1 | 9/2017 | Chuang |
| 2018/0056095 A1 | 3/2018 | Messerly et al. |
| 2018/0353191 A1 | 12/2018 | Miller et al. |
| 2020/0054350 A1 | 2/2020 | Miller |
| 2021/0045753 A1 | 2/2021 | Miller et al. |
| 2021/0052286 A1 | 2/2021 | Miller et al. |

FOREIGN PATENT DOCUMENTS

| | | |
|---|---|---|
| CA | 2454600 A1 | 2/2003 |
| CN | 2294028 Y | 10/1998 |
| CN | 2320209 Y | 5/1999 |
| CN | 2664675 Y | 12/2004 |
| DE | 10057831 A1 | 5/2002 |
| DE | 10057931 A1 | 8/2002 |
| EP | 0271775 A2 | 6/1988 |
| EP | 0517000 A2 | 12/1992 |
| EP | 0807412 A1 | 11/1997 |
| EP | 0853349 A1 | 7/1998 |
| EP | 1099450 A1 | 5/2001 |
| EP | 1314452 A1 | 5/2003 |
| EP | 1421907 A1 | 5/2004 |
| EP | 1447050 A2 | 8/2004 |
| EP | 2068725 A2 | 6/2009 |
| EP | 2177171 A1 | 4/2010 |
| EP | 3153116 A1 | 4/2017 |
| FR | 853349 A | 3/1940 |
| FR | 2457105 A1 | 12/1980 |
| FR | 2516386 A1 | 5/1983 |
| FR | 2931451 A1 | 11/2009 |
| GB | 0629824 | 9/1949 |
| GB | 2099703 A | 12/1982 |
| GB | 2130890 A | 6/1984 |
| JP | 59119808 U | 8/1984 |
| JP | 61-032633 Y2 | 9/1986 |
| JP | 61-032663 Y2 | 9/1986 |

(56) References Cited

FOREIGN PATENT DOCUMENTS

| | | | |
|---|---|---|---|
| JP | 64-052433 | A | 2/1989 |
| JP | 1052433 | A | 2/1989 |
| JP | 6132663 | A | 5/1994 |
| JP | 10-052433 | A | 2/1998 |
| JP | 2001505076 | A | 4/2001 |
| JP | 6132663 | B2 | 5/2017 |
| WO | 9208410 | A1 | 5/1992 |
| WO | 9307819 | A2 | 4/1993 |
| WO | 93/25151 | A1 | 12/1993 |
| WO | 94/07553 | A1 | 4/1994 |
| WO | 96/31164 | A1 | 10/1996 |
| WO | 9806337 | A1 | 2/1998 |
| WO | 9852638 | A2 | 11/1998 |
| WO | 99/18866 | A1 | 4/1999 |
| WO | 99/52444 | A1 | 10/1999 |
| WO | 0009024 | A1 | 2/2000 |
| WO | 00/10465 | A1 | 3/2000 |
| WO | 00/56220 | A1 | 9/2000 |
| WO | 01/78590 | A1 | 10/2001 |
| WO | 01/93931 | A1 | 12/2001 |
| WO | 02/41791 | A1 | 5/2002 |
| WO | 02/41792 | A1 | 5/2002 |
| WO | 02/096497 | A1 | 12/2002 |
| WO | 03/015637 | A1 | 2/2003 |
| WO | 2003/101307 | A1 | 12/2003 |
| WO | 2005072625 | A2 | 8/2005 |
| WO | 2005110259 | A1 | 11/2005 |
| WO | 2005112800 | A2 | 12/2005 |
| WO | 2008/033871 | A2 | 3/2008 |
| WO | 2008033874 | A2 | 3/2008 |
| WO | 2008081438 | A1 | 7/2008 |
| WO | 2009/070896 | A1 | 6/2009 |
| WO | 2011/070593 | A1 | 6/2011 |
| WO | 2011/123703 | A1 | 10/2011 |
| WO | 2012/175946 | A1 | 12/2012 |

OTHER PUBLICATIONS

Notice of Allowance issued in U.S. Appl. No. 12/427,310, dated Jun. 5, 2013 [Cited in related U.S. Appl. No. 14/532,635].
Notice of Allowance issued in U.S. Appl. No. 12/718,606, dated Mar. 6, 2013 [Cited in related U.S. Appl. No. 14/532,635].
Notice of Allowance issued in U.S. Appl. No. 12/718,606, dated Oct. 11, 2012 [Cited in related U.S. Appl. No. 14/532,635].
Notice of Allowance dated Jul. 11, 2012 in U.S. Appl. No. 12/554,708 [Cited in related U.S. Appl. No. 14/532,635].
Notification of the First Chinese Office Action, Application No. 200580003261.8, 3 pages, dated Mar. 21, 2008 [Cited in related U.S. Appl. No. 14/532,635].
Office Action (and Search Report) for European application 09150973.7, dated Oct. 23, 2009 [Cited in related U.S. Appl. No. 14/532,635].
Office Action for Chinese application 200880000182.5 (English translation), dated Jun. 27, 2013 [Cited in related U.S. Appl. No. 14/532,635].
Office Action for Chinese application 200880000182.5 (English translation), dated Sep. 10, 2010 [Cited in related U.S. Appl. No. 14/532,635].
Office Action for Chinese application 201210169456.0 with English translation, dated Aug. 28, 2013 [Cited in related U.S. Appl. No. 14/532,635].
Office Action for European application 08021732.6, dated Oct. 2, 2013 [Cited in related U.S. Appl. No. 14/532,635].
Office Action for Japanese application 2004-508,670 (English summary), dated Apr. 21, 2009 [Cited in related U.S. Appl. No. 14/532,635].
Office Action issued in Chinese Application No. 200910006631.3, dated Mar. 22, 2011 [Cited in related U.S. Appl. No. 14/532,635].
Office Communication in European Application No. 08021732.6, dated Jun. 20, 2013 [Cited in related U.S. Appl. No. 14/532,635].
Office Communication issued in Chinese Patent Application No. 200910138130.0, dated Oct. 10, 2011 [Cited in related U.S. Appl. No. 14/532,635].
Office Communication issued in European Application No. 09150973.7 dated Dec. 22, 2011 [Cited in related U.S. Appl. No. 14/532,635].
Official Action for European Application No. 03756317.8 (4 pages) dated Dec. 28, 2006 [Cited in related U.S. Appl. No. 14/532,635].
PCT International Preliminary Search Report PCT/US2005/002484, 9 pages, dated Aug. 3, 2006 [Cited in related U.S. Appl. No. 14/532,635].
PCT Invitation to Pay Additional Fees, PCT/US2007/072209, 9 pages, dated Dec. 3, 2007 [Cited in related U.S. Appl. No. 14/532,635].
Notice of Allowance in U.S. Appl. No. 11/042,912, dated Sep. 24, 2013 [Cited in related U.S. Appl. No. 14/532,635].
Notice of Allowance in U.S. Appl. No. 11/853,701, dated Oct. 11, 2013 [Cited in related U.S. Appl. No. 14/532,635].
Notice of Allowance in U.S. Appl. No. 11/853,678, dated Nov. 8, 2013 [Cited in related U.S. Appl. No. 14/532,635].
Notice of Allowance in U.S. Appl. No. 12/899,696, dated Nov. 12, 2013 [Cited in related U.S. Appl. No. 14/532,635].
Notice of Allowance in U.S. Appl. No. 12/427,310, dated Nov. 29, 2013 [Cited in related U.S. Appl. No. 14/532,635].
Notice of Allowance in U.S. Appl. No. 12/331,979, dated Dec. 23, 2013 [Cited in related U.S. Appl. No. 14/532,635].
Office Action for Canadian application 2,612,483, dated Dec. 27, 2013 [Cited in related U.S. Appl. No. 14/532,635].
Notice of Allowance dated Mar. 4, 2014 in U.S. Appl. No. 11/253,467 [Cited in related U.S. Appl. No. 14/532,635].
Notice of Allowance issued in U.S. Appl. No. 11/253,959, dated May 20, 2013 [Cited in related U.S. Appl. No. 14/532,635].
Office Action for Chinese application 201210169546.0 with English translation, dated Apr. 18, 2014 [Cited in related U.S. Appl. No. 14/532,635].
Chinese Office Action with English translation; Application No. 200780000.5; pp. 15, dated Nov. 19, 2010 [Cited in related U.S. Appl. No. 14/532,635].
Notice of Allowance in U.S. Appl. No. 11/380,340 dated Aug. 22, 2014 [Cited in related U.S. Appl. No. 14/532,635].
Notice of Allowance in U.S. Appl. No. 14/721,144 dated Jul. 22, 2014 [Cited in related U.S. Appl. No. 14/532,635].
Notice of Allowance in U.S. Appl. No. 11/619,390 dated Jul. 3, 2014 [Cited in related U.S. Appl. No. 14/532,635].
Notice of Allowance in U.S. Appl. No. 11/619,390 dated Nov. 6, 2014 [Cited in related U.S. Appl. No. 14/532,635].
Notice of Allowance in U.S. Appl. No. 12/259,745 dated Nov. 7, 2014 [Cited in related U.S. Appl. No. 14/532,635].
Notice of Allowance in U.S. Appl. No. 12/718,638, dated Aug. 3, 2015 [Cited in related U.S. Appl. No. 14/532,635].
Notice of Allowance in U.S. Appl. No. 13/966,104, dated Aug. 17, 2015 [Cited in related U.S. Appl. No. 14/532,635].
"Proven reliability for quality bone marrow samples", Special Procedures, Cardinal Health, 6 pages, 2003 [Cited in related U.S. Appl. No. 14/532,635].
Astrom, K. Gunnar O., "CT-guided Transsternal Core Biopsy of Anterior Mediastinal Masses," Radiology 1996; 199:564-567 [Cited in related U.S. Appl. No. 14/532,635].
Astrom, K.G., "Automatic Biopsy Instruments Used Through a Coaxial Bone Biopsy System with an Eccentric Drill Tip," Acta Radiologica, 1995; 36:237-242 [Cited in related U.S. Appl. No. 14/532,635].
BioAccess.com, Single Use Small Bone Power Tool—How It Works, 1 pg, printed Jun. 9, 2008 [Cited in related U.S. Appl. No. 14/532,635].
Buckley et al., CT-guided bone biopsy: Initial experience with commercially available hand held Black and Decker drill, European Journal of Radiology 61, pp. 176-180, 2007 [Cited in related U.S. Appl. No. 14/532,635].
F.A.S.T. 1 Intraosseous Infusion System with Depth-Control Mechanism Brochure, 6 pages, 2000 [Cited in related U.S. Appl. No. 14/532,635].
Gunal et al., Compartment Syndrome After Intraosseous Infusion: An Experimental Study in Dogs, Journal of Pediatric Surgery, vol. 31, No. 11, pp. 1491-1493, Dated Nov. 1996 [Cited in related U.S. Appl. No. 14/532,635].

(56) References Cited

OTHER PUBLICATIONS

Hakan et al., CT-guided Bone Biopsy Perfomied by Means of Coaxial Biopsy System with an Eccentric Drill, Radiology, pp. 549-552, 1993 [Cited in related U.S. Appl. No. 14/532,635].

Liakat A. Parapia, Trepanning or trephines: a history of bone marrow biopsy, British Journal of Haematology, pp. 14-19, 2007 [Cited in related U.S. Appl. No. 14/532,635].

Michael Trotty, "Technology (A Special Report), The Wall Street Journal 2008 Technology Innovation Awards This year's winners include: an IV alternative, a better way to make solar panels, a cheap, fuel efficient car and a better way to see in the dark", The Wall Street Journal, Factiva, 5 pages, 2008 [Cited in related U.S. Appl. No. 14/532,635].

Pediatric Emergency, Intraosseous Infusion for Administration of Fluids and Drugs, www.cookgroup.com, 1 pg, 2000 [Cited in related U.S. Appl. No. 14/532,635].

Pediatrics, 2005 American Heart Association Guidelines for Cardiopulmonary Resuscitation and Emergency Cardiovascular Care of Pediatric and Neonatal Patients: Pediatric Advanced Life Support, Downloaded from www.pediatrics.org, printed Feb. 21, 2007 [Cited in related U.S. Appl. No. 14/532,635].

Richard O. Cummings et al., "ACLS—Principles and Practice", ACLS—The Reference Textbook, American Heart Association, pp. 214-218. 2003 [Cited in related U.S. Appl. No. 14/532,635].

Riley et al., "A Pathologist's Perspective on Bone Marrow Aspiration Biopsy: I. Performing a Bone Marrow Examination," Journal of Clinical Laboratory Analysis 18, pp. 70-90, 2004 [Cited in related U.S. Appl. No. 14/532,635].

Vidacare Corporation Comments to Intraosseous Vascular Access Position Paper, Infusion Nurses Society, 6 pages, dated May 4, 2009 [Cited in related U.S. Appl. No. 14/532,635].

Australian Exam Report on Patent Application No. 2003240970, 2 pages, dated Oct. 15, 2007 [Cited in related U.S. Appl. No. 14/532,635].

Chinese Office Action with English translation; Application No. 200780001198.3; pp. 13; dated Apr. 27, 2010 [Cited in related U.S. Appl. No. 14/532,635].

Communication Pursuant to Article 94(3) EPC, Application No. 05 712 091.7-1265, 4 pages, dated Apr. 8, 2008 [Cited in related U.S. Appl. No. 14/532,635].

Communication relating to the results of the partial International Search Report for PCT/US2005/002484, 6 pages, dated May 19, 2005 [Cited in related U.S. Appl. No. 14/532,635].

European Office Action Communication, Application No. 08158699.2-1265/1967142, 10 pages, dated Nov. 4, 2008 [Cited in related U.S. Appl. No. 14/532,635].

European Office Action EP03731475.4, 4 pages, dated Oct. 11, 2007 [Cited in related U.S. Appl. No. 14/532,635].

European Office Action dated Jan. 19, 2011 and Response dated Jul. 21, 2011 , EP Application No. 09150973.7 [Cited in related U.S. Appl. No. 14/532,635].

European Office Action dated Dec. 22, 2011 and Response dated Jun. 29, 2012 , EP Application No. 09150973.7 [Cited in related U.S. Appl. No. 14/532,635].

European Search Report 08158699.2-1265, 4 pages, dated Aug. 2008 [Cited in related U.S. Appl. No. 14/532,635].

International PCT Search Report and Written Opinion PCT/US2004/037753, 16 pages, dated Jul. 8, 2005 [Cited in related U.S. Appl. No. 14/532,635].

International PCT Search Report and Written Opinion PCT/US2005/002484, 15 pages, dated Jul. 22, 2005 [Cited in related U.S. Appl. No. 14/532,635].

International PCT Search Report PCT/US03/17167, 8 pages, dated Sep. 16, 2003 [Cited in related U.S. Appl. No. 14/532,635].

International PCT Search Report PCT/US03/17203, 8 pages, dated Sep. 16, 2003 [Cited in related U.S. Appl. No. 14/532,635].

International PCT Search Report PCT/US2004/037753, 6 Pages, dated Apr. 19, 2005 [Cited in related U.S. Appl. No. 14/532,635].

International Preliminary Report on Patentability for international application PCT/US2007/072202. dated Jan. 15, 2009 [Cited in related U.S. Appl. No. 14/532,635].

International Preliminary Report on Patentability, PCT/US/2007/078203, 13 pages, dated Mar. 26, 2009 [Cited in related U.S. Appl. No. 14/532,635].

International Preliminary Report on Patentability, PCT/US08/52943, 7 pages, dated Oct. 15, 2009 [Cited in related U.S. Appl. No. 14/532,635].

International Search Report and Written Opinion, PCT/US08/500346, 12 pages, dated May 22, 2008 [Cited in related U.S. Appl. No. 14/532,635].

International Search Report and Written Opinion, PCT/US08/52943, 8 pages, dated Sep. 26, 2008 [Cited in related U.S. Appl. No. 14/532,635].

International Search Report and Written Opinion, PCT/US2007/072202, 17 pages, dated Mar. 25, 2008 [Cited in related U.S. Appl. No. 14/532,635].

International Search Report and Written Opinion, PCT/US2007/078204, 14 pages, dated May 15, 2008 [Cited in related U.S. Appl. No. 14/532,635].

International Search Report and Written Opinion, PCT/US2007/078203, 15 pages, dated May 13, 2008 [Cited in related U.S. Appl. No. 14/532,635].

International Search Report and Written Opinion, PCT/US2007/078207, 13 pages, dated Apr. 7, 2008 [Cited in related U.S. Appl. No. 14/532,635].

International Search Report and Written Opinion, PCT/US2007/078205, 13 pages, dated Sep. 11, 2007 [Cited in related U.S. Appl. No. 14/532,635].

International Search Report w/Written Opinion, PCT/US2006/025201, 18 pgs, dated Jan. 29, 2007 [Cited in related U.S. Appl. No. 14/532,635].

International Search Report, PCT/US2006/025201, 12 pages, dated Feb. 7, 2008 [Cited in related U.S. Appl. No. 14/532,635].

International Search Report, PCT/US2007/072209, 18 pages, dated Apr. 25, 2008 [Cited in related U.S. Appl. No. 14/532,635].

International Search Report, PCT/US2007/072217, 20 pages, dated Mar. 31, 2008 [Cited in related U.S. Appl. No. 14/532,635].

Japanese Office Action with English Translation; Application No. 2004-508,670; PCT/US03/17203; pp. 7; dated Jan. 20, 2011 [Cited in related U.S. Appl. No. 14/532,635].

Notice of Allowance in U.S. Appl. No. 11/620,927 dated Jun. 3, 2014 [Cited in related U.S. Appl. No. 14/532,635].

Notice of Allowance in U.S. Appl. No. 12/407,651 dated Jun. 11, 2014 [Cited in related U.S. Appl. No. 14/532,635].

Notice of Allowance issued in U.S. Appl. No. 11/042,912, dated Mar. 27, 2013 [Cited in related U.S. Appl. No. 14/532,635].

Notice of Allowance issued in U.S. Appl. No. 11/042,912, dated Oct. 5, 2012 [Cited in related U.S. Appl. No. 14/532,635].

Notice of Allowance issued in U.S. Appl. No. 11/253,959, dated Mar. 14, 2013 [Cited in related U.S. Appl. No. 14/532,635].

Notice of Allowance issued in U.S. Appl. No. 11/853,678, dated Mar. 27, 2013 [Cited in related U.S. Appl. No. 14/532,635].

Chineese Office Action with English translation; Application No. 200910006631.3; pp. 12, dated Mar. 11, 2010.

Chinese Office Action w/english translation; Application No. 200680021872.X; pp. 8, dated Nov. 6, 2009.

Chinese Office Action with English translation, Application No. 2005800003261, 9 pgs, dated Jan. 16, 2009.

Chinese Office Action with English translation; Application No. 200380000022.0; pp. 10; dated Dec. 13, 2010.

Chinese Office Action with English translation; Application No. 200780001190.7; 12 pgs., dated Jun. 2, 2010.

Chinese Office Action with English translation; Application No. 200780001196; 12 pgs., dated Jul. 12, 2010.

Chinese Office Action with English translation; Application No. 200830000022.0; pp. dated May 25, 2012.

Chinese Office Action with English translation; Application No. 200880000022.0; Pgs. Dated Sep. 22, 2011.

Chinese Office Action with English translation; Application No. 200910006631.3; pp. 9, dated Nov. 11, 2010.

(56) References Cited

OTHER PUBLICATIONS

Chinese Office Action, Application No. 200780000590.6, (with English translation), (13 pages), dated Aug. 21, 2009.
Chinese Office Action, Application No. 200780001188.X, (with English translation), (8 pgs) dated Nov. 9, 2010.
Chinese Office Action, Notification of the Fourth Office Action, Application No. 200880000022.0, dated Jan. 7, 2013.
Chinese Office Action, Notification of the Second Office Action, Application No. 200780000590.6, dated Mar. 1, 2010.
Edited by Frederick A. Matsen III M.D., Compartmental Syndromes, About Compartmental Syndromes, Generic Trauma Content http://www.orthop.washington.edu/uw/.., pp. 1-45.
European Extended Search Report, Application No. EP08021732.6, 7 pages, dated Nov. 13, 2009.
European Extended Search Report, Application No. EP10153350.3, 5 pages, dated Mar. 11, 2010.
European Office Action dated Apr. 8, 2008 and Response dated May 15, 2008 , EP Application No. 05712091.7.
European Office Action dated Feb. 21, 2007 and Response dated Jun. 27, 2007 , EP Application No. 05712091.7.
European Office Action dated Sep. 21, 2007 and Response dated Nov. 26, 2007, EP Application No. 05712091.7.
European Office Action dated Sep. 8, 2010 and Response dated Mar. 17, 2011, EP Application No. 10153350.3.
European Office Action, Application No. 10 153 350.3, 5 pages, dated Sep. 8, 2010.
European Patent Office, Communication from Examining Division for European Patent Application No. 08799753.2, dated Apr. 10, 2014.
European Patent Office, Communication from Examining Division for European Patent Application No. 08799753.2, dated May 18, 2015.
European Patent Office, Communication from Examining Division for European Patent Application No. 08799753.2, dated Sep. 29, 2014.
European Patent Office, European Search Report for European Patent Application No. 08799753.2, dated May 23, 2013.
European Search Report for European Patent Application No. 07842288.8, dated Mar. 16, 2011.
European Search Report issued in European Patent Application No. 17198059.2 dated Jan. 29, 2018.
European Telephone Consultation Report dated Apr. 21, 2009 and Response dated Jun. 24, 2009 , EP Application No. 08158699 .2.
European Telephone Consultation Report dated Sep. 23, 2009 and Response dated Oct. 28, 2009 , EP Application No. 08158699 .2.
Extended European Search Report for European application 07842285.4. dated Mar. 17, 2011.
Extended European Search Report for European application 07842286.2. dated Mar. 18, 2011.
Final Office Action, U.S. Appl. No. 11/064,156, 12 pages, dated Jun. 19, 2009.
Final Office Action, U.S. Appl. No. 11/781,568, 19 pages, dated Jun. 17, 2009.
Final Office Action, U.S. Appl. No. 11/781,597, 14 pages, dated Nov. 17, 2009.
Final Office Action, U.S. Appl. No. 11/853,685, 21 pages, dated Jun. 24, 2009.
International Preliminary Report on Patentability for international application PCT/US2007/078204, dated Apr. 2, 2009.
International Preliminary Report on Patentability for international application PCT/US2007/078205, dated Mar. 26, 2009.
International Preliminary Report on Patentability for international application PCT/US2007/078207, dated Mar. 26, 2009.
International Preliminary Report on Patentability in International Application No. PCT/US/2007/072209, dated May 14, 2009.
International Preliminary Report on Patentability in International Application No. PCT/US/2008/050346, dated Jul. 23, 2009.
International Preliminary Report on Patentability in International Application No. PCT/US2007/072217 dated Feb. 12, 2009.
International Search Report and Written Opinion for international application PCT/US2008/050346 , dated May 22, 2008.
International Search Report and Written Opinion issued in PCT/US2014/028594, dated Jul. 28, 2014.
Interview Summary dated Jul. 13, 2009 and Response to Interview Summary and Amendment filed Aug. 12, 2009, U.S. Appl. No. 11/190,331, 17 pages.
Japanese Office Action, Application No. 2004-508669, (with English summary), (9 pages), dated Aug. 3, 2009.
Non-Final Office Action dated Apr. 1, 2009 and Response to Office Action filed Jul. 1, 2009, U.S. Appl. No. 10/449,503, 19 pages.
Non-Final Office Action dated Mar. 23, 2009 and Response to Office Action filed Jun. 22, 2009, U.S. Appl. No. 11/190,331, 61 pages.
Non-Final Office Action dated May 29, 2009 and Response to Office Action filed Aug. 12, 2009, U.S. Appl. No. 10/449,476, 20 pages.
Non-Final Office Action, U.S. Appl. No. 10/449,476, 8 pages, dated Oct. 29, 2008.
Non-Final Office Action, U.S. Appl. No. 10/987,051, 9 pages, dated Nov. 10, 2009.
Non-Final Office Action, U.S. Appl. No. 11/042,912, 8 pages, dated Jul. 23, 2009.
Non-Final Office Action, U.S. Appl. No. 12/259,745,11 pages, dated Jul. 17, 2009.
Notice of Allowance dated Jun. 22, 2012 in U.S. Appl. No. 11/042,912.
Notice of Allowance dated Mar. 27, 2013 in U.S. Appl. No. 11/042,912.
Notice of Allowance in U.S. Appl. No. 11/253,467, dated Jun. 24, 2014.
Notice of Allowance in U.S. Appl. No. 11/853,678 dated Jul. 11, 2013.
Notice of Allowance in U.S. Appl. No. 11/853,678, dated Oct. 11, 2013.
Notice of Allowance in U.S. Appl. No. 11/853,701 dated Jul. 3, 2013.
Notice of Allowance in U.S. Appl. No. 12/331,979 dated Jul. 17, 2013.
Notice of Allowance in U.S. Appl. No. 12/899,696 dated Aug. 27, 2013.
Notice of Allowance in U.S. Appl. No. 12/899,696 dated Jul. 18, 2013.
Notice of Allowance issued in U.S. Appl. No. 11/253,467, dated Mar. 29, 2013.
Notice of Allowance issued in U.S. Appl. No. 12/554,664 dated Jul. 20, 2012.
Notification of First Chinese Office Action, Application No. 201410112780.9, dated May 27, 2015.
Office Action for European application 07842284.7. dated May 3, 2012.
Office Action for European application 07842285.4. dated May 3, 2012.
Office Action for European application 07842286.2. dated Apr. 30, 2012.
Office Action for European application 07842288.8. dated May 3, 2012.
Office Action for Japanese Application No. 2004-508670 with English Translation, dated Aug. 31, 2010.
Office Action for Taiwanese application 093134480 (English Translation), dated Feb. 11, 2011.
Office Action for U.S. Appl. No. 11/042,912, dated Mar. 19, 2010.
Office Action for U.S. Appl. No. 11/042,912, dated Nov. 28, 2008.
Office Action for U.S. Appl. No. 11/190,331, dated Mar. 23, 2009.
Office Action for U.S. Appl. No. 11/253,467, dated Apr. 28, 2011.
Office Action for U.S. Appl. No. 11/253,467, dated Jul. 22, 2010.
Office Action for U.S. Appl. No. 11/253,467, dated Oct. 29, 2010.
Office Action for U.S. Appl. No. 11/253,959, dated Aug. 5, 2010.
Office Action for U.S. Appl. No. 11/253,959, dated Mar. 30, 2011.
Office Action for U.S. Appl. No. 11/253,959, dated Oct. 18, 2010.
Office Action for U.S. Appl. No. 11/427,501, dated Aug. 7, 2008.
Office Action for U.S. Appl. No. 11/427,501, dated Oct. 21, 2009.
Office Action for U.S. Appl. No. 11/427,501. dated May 13, 2009.
Office Action for U.S. Appl. No. 12/905,659, dated Mar. 21, 2011.
Office Action for U.S. Appl. No. 12/905,659, dated May 13, 2011.

(56) References Cited

OTHER PUBLICATIONS

Office Action in Canadian Patent Application No. 2,612,433, dated Aug. 22, 2014.
Office Action in Canadian Patent Application No. 2,612,483, dated Aug. 22, 2014.
Office Action issued in Chinese Patent Application No. 201010144512.7, dated Feb. 23, 2011.
Office Action issued in Chinese Patent Application No. 201010144520.1, dated Jan. 27, 2011.
Office Action issued in European Application No. 09155111.9 dated Nov. 25, 2009.
Office Communication for European application 09150973.7-1269, dated Jan. 19, 2011.
Office Communication for European Patent Application No. 07842288.8, dated Mar. 12, 2015.
Office Communication in European Application No. 10153350.3, dated Jun. 14, 2011.
Office Communication issued in Taiwanese Patent Application No. 093134480, dated Jan. 15, 2011.
PCT Invitation to pay additional fees for international application PCT/US2006/025201, dated Oct. 26, 2006.
Request for Continued Examination and Amendment for U.S. Appl. No. 11/731,568, filed Sep. 17, 2009.
Request for Continued Examination and Amendment, U.S. Appl. No. 11/064,156, 22 pages, dated Nov. 19, 2009.
Response to Extended European Search Report in European Application No. 10153350.3, filed Jun. 30, 2010.
Response to Non-Final Office Action, U.S. Appl. No. 11/042,912, (11 pgs.), dated Oct. 23, 2009.
Response to Office Action for European application 07842284.7. filed Nov. 10, 2012.
Response to Office Action for European application 07842285.4. filed Nov. 13, 2012.
U.S. Appl. No. 10/449,476, filed May 30, 2003.
U.S. Appl. No. 11/253,467, filed Oct. 19, 2005.
U.S. Appl. No. 14/532,635, filed Nov. 4, 2014.
U.S. Appl. No. 16/664,282, filed Oct. 25, 2019.
Response to Office Action for European application 07842286.2. filed Nov. 8, 2012.
Response to Office Action for European application 07842288.8. filed Nov. 9, 2012.
Response to Office Action for U.S. Appl. No. 10/449,476, filed Aug. 12, 2009.
Response to Office Action for U.S. Appl. No. 11/427,501, filed Jul. 1, 2009.
Response to Office Communication in European Application No. 10153350.3, filed Feb. 9, 2012.
Response to Official Letter for European application 07842284.7. filed Oct. 14, 2011.
Response to Official Letter for European application 07842285.4. filed Oct. 14, 2011.
Response to Official Letter for European application 07842286.2. filed Oct. 14, 2011.
Response to Official Letter for European application 07842288.8. filed Oct. 14, 2011.
State Intellectual Property Office of the People's Republic of China, Notification of the Second Office Action for Chinese Application No. 200880000182.5, dated Mar. 12, 2012.
State Intellectual Property Office of the People's Republic of China, Notification of the Third Office Action for Chinese Application No. 200680000182.5, dated Dec. 13, 2012.
State Intellectual Property Office of the People's Republic of China, Reexamination Decision for Chinese Application No. 200880000182.5, dated Nov. 20, 2013.
Taiwan Office Action, Application No. 94102179 (with English translation); 12 pages, dated May 13, 2010.

* cited by examiner

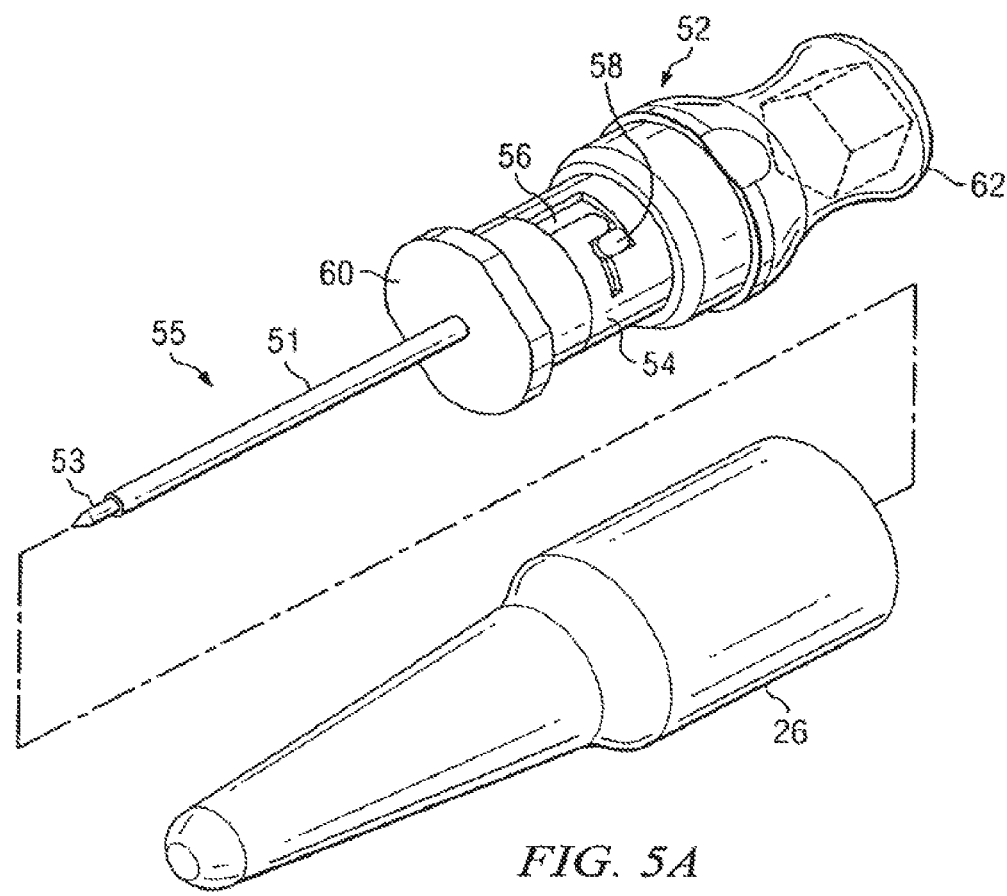
FIG. 5A
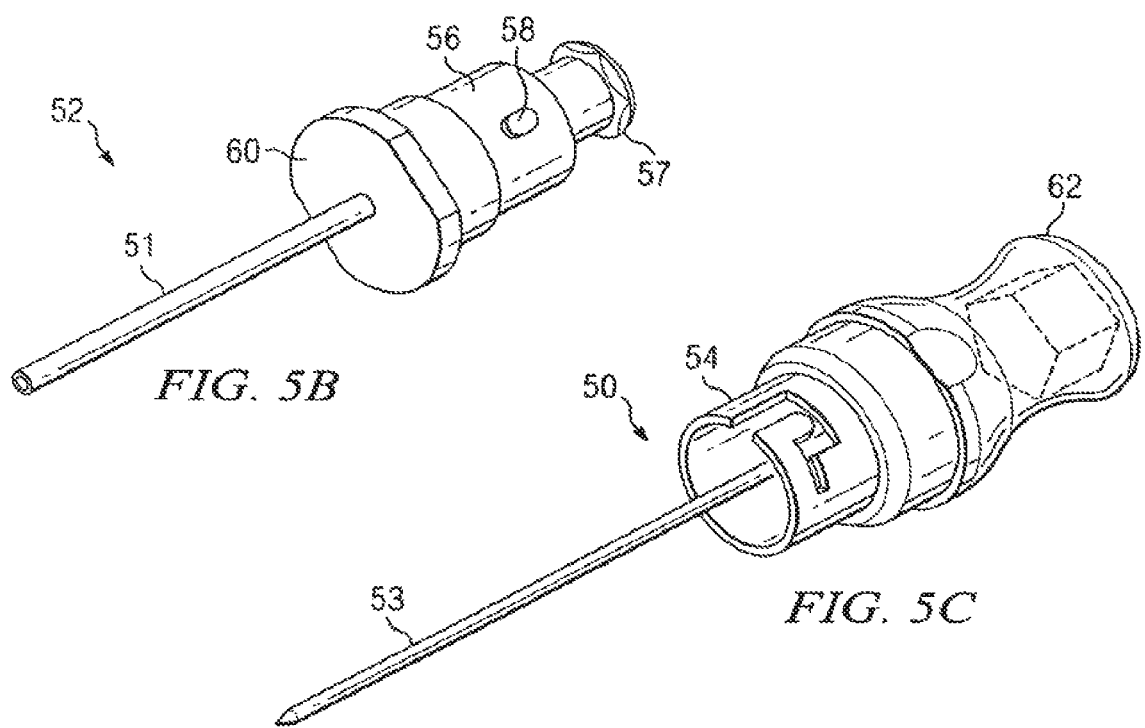
FIG. 5B
FIG. 5C

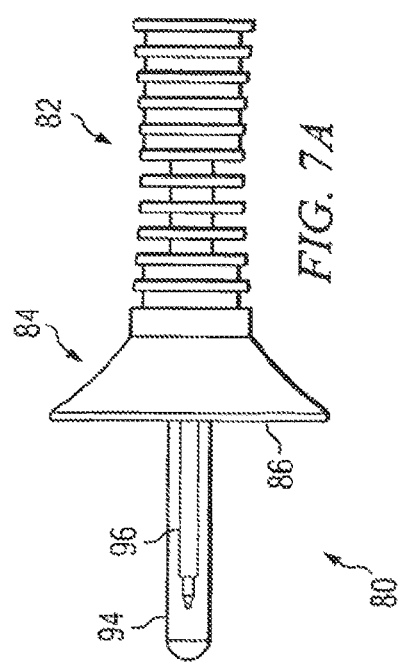
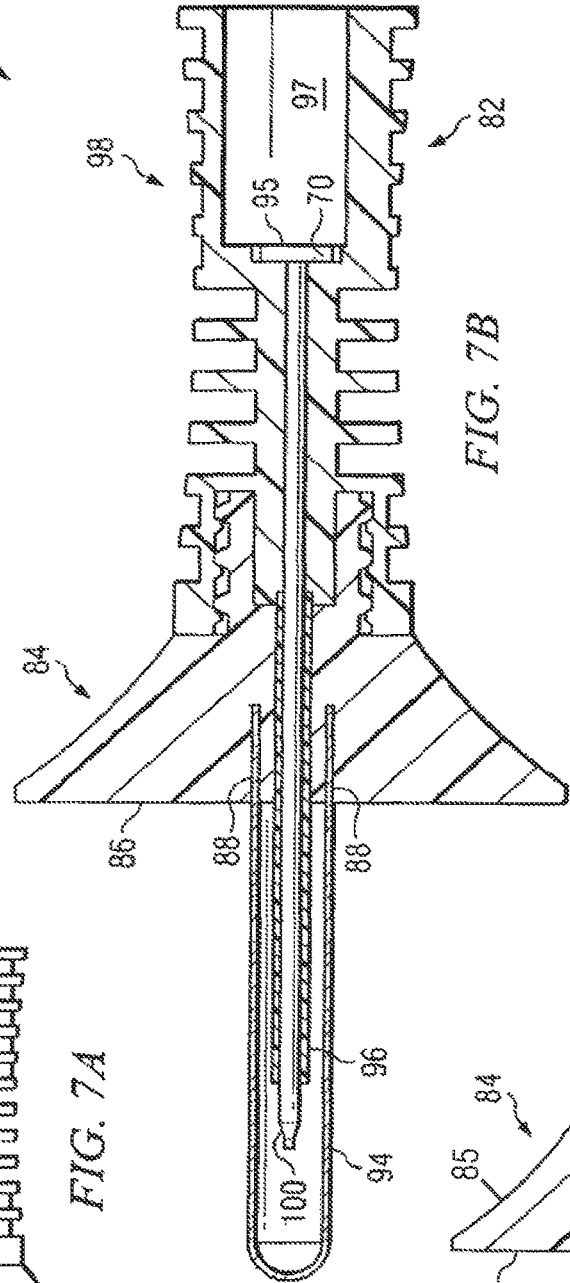
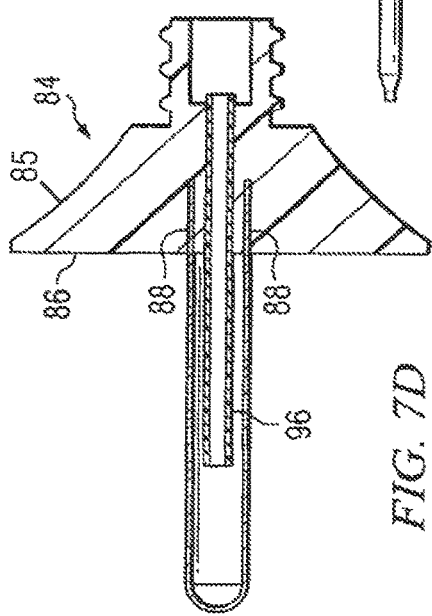
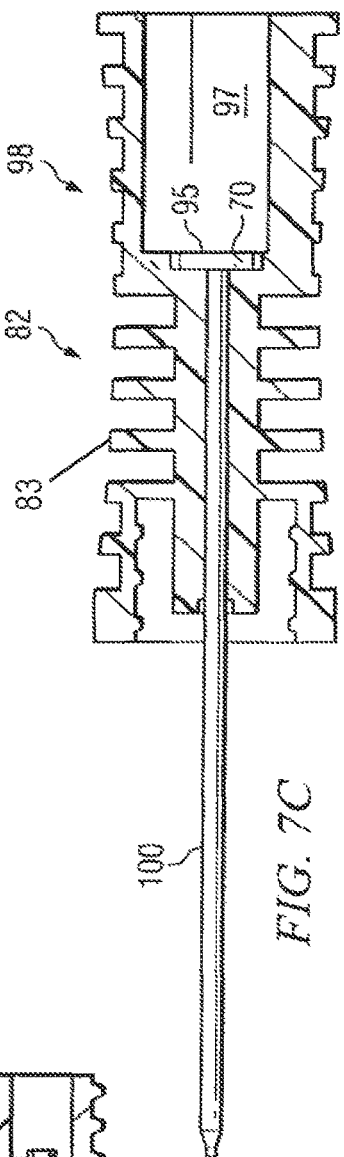

APPARATUS AND METHOD TO ACCESS BONE MARROW

RELATED APPLICATION

This application is a continuation of U.S. patent application Ser. No. 16/664,282, filed Oct. 25, 2019, and entitled "Apparatus and Method to Access Bone marrow", which is a continuation of U.S. patent application Ser. No. 14/532,635, filed Nov. 4, 2014, and entitled "Apparatus and Method to Access Bone Marrow", now U.S. Pat. No. 10,456,149, which is a continuation of U.S. patent application Ser. No. 11/253,467, filed Oct. 19, 2005, and entitled "Apparatus and Method to Access Bone Marrow", now U.S. Pat. No. 8,876,826, which is a divisional application of U.S. patent application Ser. No. 10/449,476, filed May 30, 2003, and entitled "Apparatus and method to Access Bone marrow", now U.S. Pat. No. 7,699,850, which claims priority to U.S. Provisional Patent Application Ser. No. 60/384,756, filed May 31, 2002, and entitled "Apparatus and method to Provide Access Bone Marrow." The contents of each of the above-identified disclosures are incorporated hereby in their entirety by reference.

TECHNICAL FIELD

The present invention is related in general to a medical device to access the bone marrow and specifically to an apparatus and method for penetrating the bone marrow with a powered drill and inserting a penetrator or needle.

BACKGROUND OF THE INVENTION

Every year, millions of patients are treated for life-threatening emergencies in the United States. Such emergencies include shock, trauma, cardiac arrest, drug overdoses, diabetic ketoacidosis, arrhythmias, burns, and status epilepticus just to name a few. For example, according to the American Heart Association, more than 1,500,000 patients suffer from heart attacks (myocardial infarctions) every year, with over 500,000 of them dying from its devastating complications.

An essential element for treating all such emergencies is the rapid establishment of an intravenous (IV) line in order to administer drugs and fluids directly into the circulatory system. Whether in the ambulance by paramedics, or in the emergency room by emergency specialists, the goal is the same—to start an IV in order to administer life-saving drugs and fluids. To a large degree, the ability to successfully treat such critical emergencies is dependent on the skill and luck of the operator in accomplishing vascular access. While it is relatively easy to start an IV on some patients, doctors, nurses and paramedics often experience great difficulty establishing IV access in approximately 20 percent of patients. These patients are probed repeatedly with sharp needles in an attempt to solve this problem and may require an invasive procedure to finally establish an intravenous route.

A further complicating factor in achieving IV access occurs "in the field" e.g. at the scene of an accident or during ambulance transport where it is difficult to see the target and excessive motion make accessing the venous system very difficult.

In the case of patients with chronic disease or the elderly, the availability of easily-accessible veins may be depleted. Other patients may have no available IV sites due to anatomical scarcity of peripheral veins, obesity, extreme dehydration or previous IV drug use. For these patients, finding a suitable site for administering lifesaving drugs becomes a monumental and frustrating task. While morbidity and mortality statistics are not generally available, it is known that many patients with life-threatening emergencies have died of ensuing complications because access to the vascular system with life-saving IV therapy was delayed or simply not possible. For such patients, an alternative approach is required.

SUMMARY OF THE INVENTION

In accordance with teachings of the present invention, an apparatus and method for gaining rapid access to the bone marrow is provided.

In one embodiment of the invention an apparatus for penetrating a bone marrow is provided that includes a housing and a penetrator assembly. The penetrator assembly is operable to penetrate the bone marrow, having a removable inner trocar and an outer penetrator. A connector operable to releasably attach the penetrator assembly to a drill shaft is included. The drill shaft is operable to connect the penetrator assembly to a gear assembly. The gear assembly is operable to engage and rotate the drill shaft. A motor operable to engage the gear assembly and drive the penetrator into the bone marrow by rotation of the drill shaft and a power supply and associated circuitry operable to power the motor are also included.

In another embodiment of the invention an apparatus for penetrating a bone marrow is provided that includes a housing and a penetrator assembly, operable to penetrate the bone marrow. A connector operable to releasably attach the penetrator assembly to a drill shaft, the drill shaft operable to connect the penetrator assembly to a reduction gear assembly is included. A reduction gear assembly operable to engage and rotate the drill shaft and a motor operable to engage the reduction gear assembly and drive the penetrator into the bone marrow by rotation of the drill shaft are also included. A power supply and associated circuitry operable to power the motor are also provided.

In one embodiment of the invention a penetrator assembly operable to provide access to a bone marrow comprising an outer penetrator and a removable inner trocar operable to penetrate the bone marrow is provided A connector operable to releasably attach the penetrator assembly to a power drill is also included.

In another embodiment of the invention a penetrator assembly operable to provide access to a bone marrow comprising an outer penetrator and a removable inner trocar operable to penetrate the bone marrow is provided. The inner trocar includes a handle, the handle including a grasping means that allows a user to grasp and manipulate the device. The outer penetrator includes a handle, the handle including a grasping means, and also includes a flange operable to engage an insertion site proximate the bone marrow. A connector operable to releasably attach the penetrator assembly to a power drill is also provided. The inner trocar is operable to releasably engage the connector.

In one embodiment of the current invention a method of accessing a bone marrow is provided that includes inserting a penetrator assembly into the bone marrow by means of a powered apparatus, detaching the powered apparatus from the penetrator, removing an inner trocar from an outer penetrator of the assembly and attaching a right angle connector to the outer penetrator.

In another embodiment of the current invention a method of accessing a bone marrow is provided that includes inserting a penetrator assembly into the bone marrow by means of a powered apparatus, detaching the powered apparatus from the penetrator, removing an inner trocar from an outer penetrator of the assembly and attaching an adapter suitable to convey medications or fluids to the bone marrow.

In yet another embodiment of the current invention a method of manufacturing an apparatus operable to penetrate a bone marrow is provided that includes manufacturing a housing having a connector operable to releasably attach a penetrator assembly to a drill shaft, a drill gear assembly, a gear assembly operable to engage and rotate the drill shaft, a motor operable to engage the gear assembly and drive a penetrator assembly into the bone marrow and a power supply and associated circuitry operable to power the motor and manufacturing a penetrator assembly operable to releasably attach to the connector.

In a further embodiment of the current invention, a kit for use in penetrating a bone marrow in an extremity is provided that includes a carrying case, an apparatus for penetrating the bone marrow including a housing and penetrator assemblies operable to penetrate the bone marrow, a removable inner trocar and an outer penetrator forming portions of at least one of the penetrator assemblies, at least one, connector operable to releasably attach the penetrator assemblies to a drill shaft, a gear assembly operable to engage and rotate the drill shaft, a motor operable to engage the reduction gear assembly and drive at least one of the penetrator assemblies into the bone marrow and a power supply and associated circuitry to power the motor and a strap operable to immobilize the outer penetrator to a site in an extremity.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein

FIG. 5A-C illustrates one embodiment of a penetrator assembly of the present invention;

FIG. 7A illustrates one embodiment of a penetrator assembly of the present invention;

FIG. 7B illustrates a cross-sectional view of one embodiment of a penetrator assembly of the present invention;

FIG. 7C illustrates one embodiment of an inner trocar in cross section of the present invention;

FIG. 7D illustrates one embodiment of an outer penetrator in cross section of the present invention.

DETAILED DESCRIPTION OF THE INVENTION

Preferred embodiments of the invention and its advantages are best understood by reference to FIGS. 1A-10 wherein like numbers refer to same and like parts.

Figure 1A:
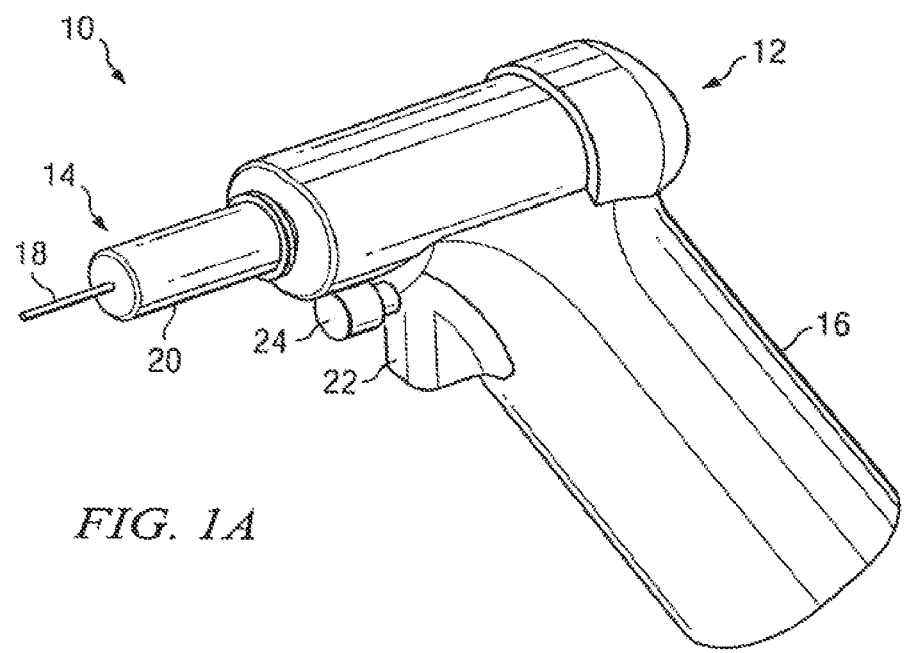
FIG. 1A is a schematic drawing showing an isometric view of one embodiment of the present invention.
Figure 1B:
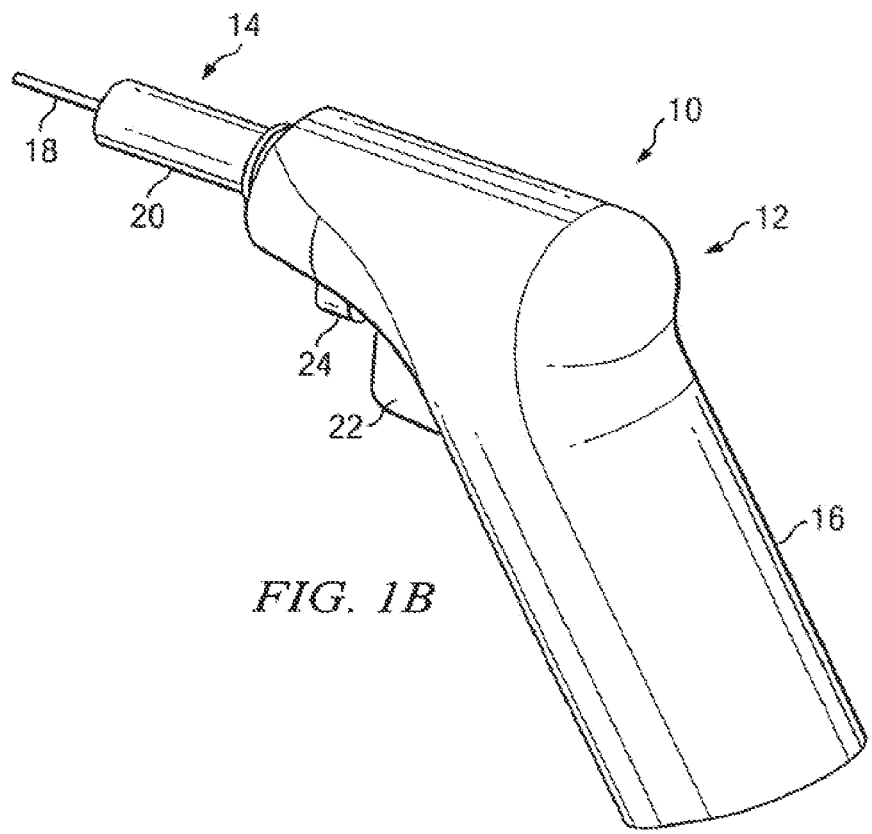
FIG. 1B is a schematic drawing showing an isometric view of one embodiment of the present invention.

Various examples of an apparatus operable to access the bone marrow in accordance with the present invention are shown generally in FIGS. 1A and 12 at 10. Apparatus 10 as shown in FIGS. 1A and 1B generally includes housing 12 and penetrator assembly 14. Housing 12 includes handle 16 that is sized and contoured to fit the hand of an operator. Handle 16 may include on/off switch 22 and safety 24. Penetrator assembly 14 includes outer penetrator 18, inner trocar (not expressly shown) and penetrator assembly connector 20.

Figure 2A:
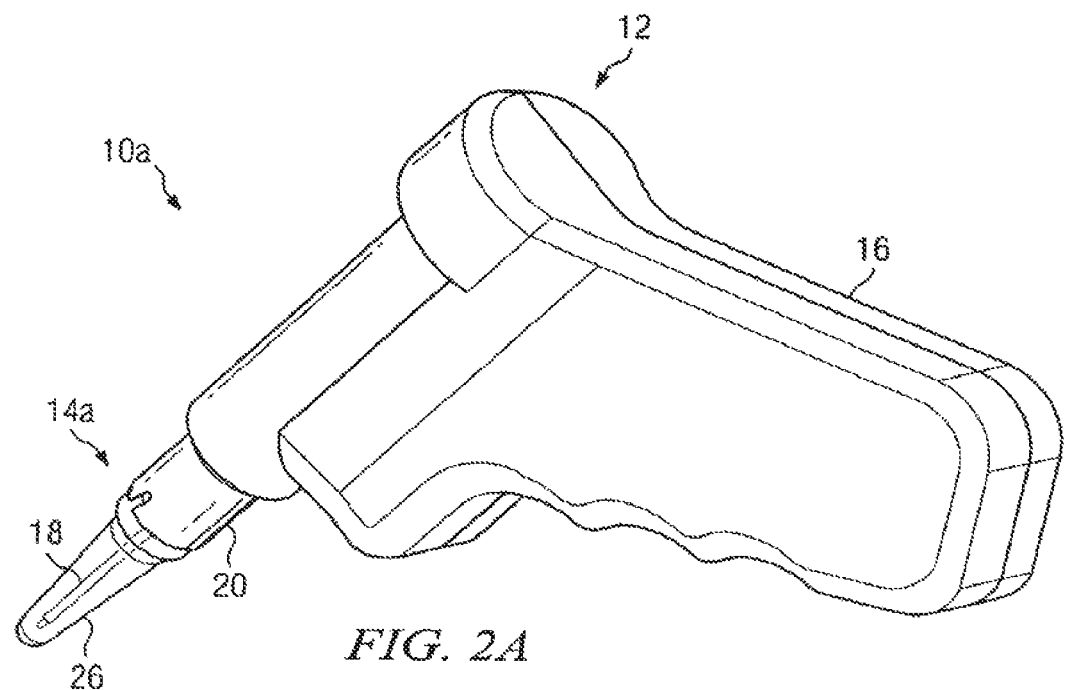
FIG. 2A is a schematic drawing showing an isometric view of one embodiment of the present invention.
Figure 2B:
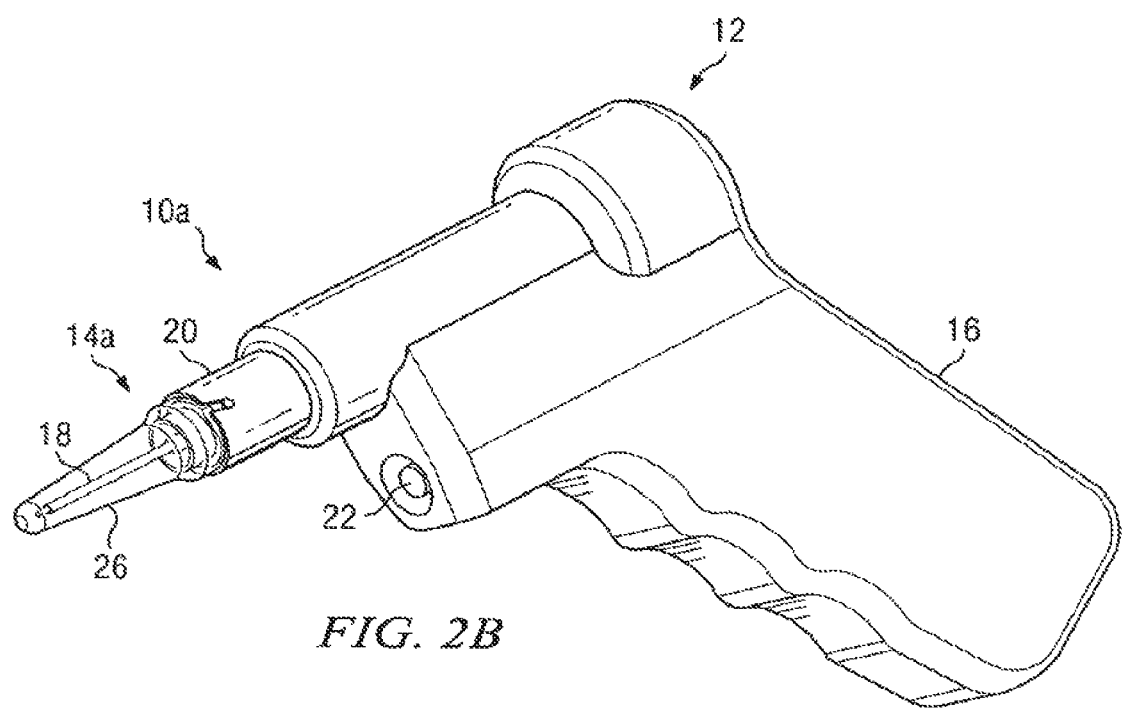
FIG. 2B is a schematic drawing showing an isometric view of one embodiment of the present invention.

FIGS. 2A and 2B illustrate an alternate embodiment of the present invention. Apparatus 10a generally includes housing 12 and penetrator assembly 14a. Housing 12 includes handle 16 that is sized and contoured to fit the hand of an operator. Handle 16 may include an on/off switch 22. Penetrator assembly 14a includes outer penetrator 18, inner trocar (not expressly shown) and penetrator assembly connector 20. Penetrator assembly 14a may include penetrator shield 26. An outer penetrator may include either a trocar, a needle, a cannula, a hollow tube, a drill bit or a hollow drill bit.

Figure 3A:
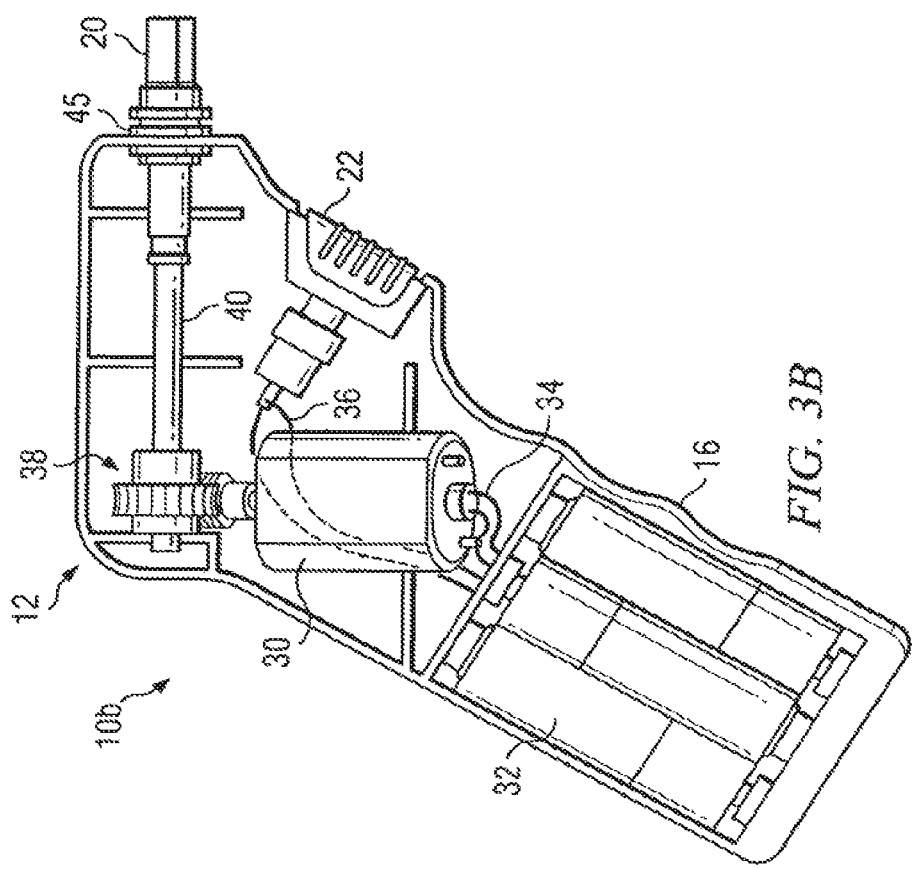
FIG. 3A-C illustrates a side and cross-sectional view of one embodiment of the present invention.
Figure 3B:
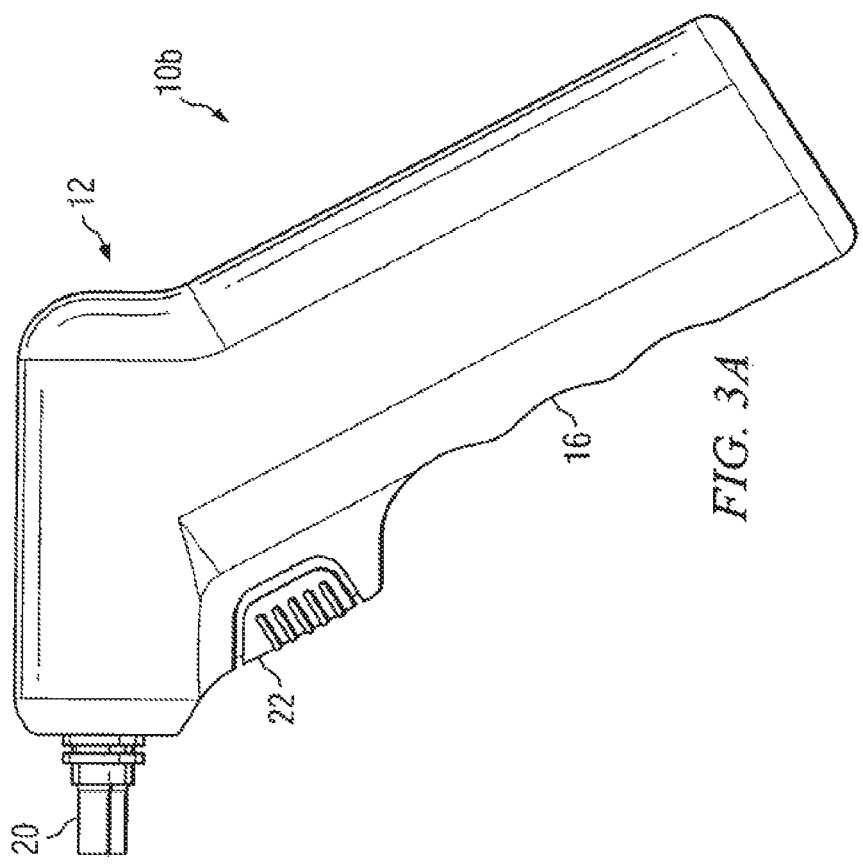
Figure 3C:
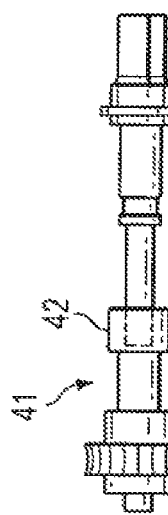

FIGS. 3A and 3B illustrate yet another embodiment of the present invention. Apparatus 10b generally includes housing 12 and a penetrator assembly (not expressly shown). Housing 12 includes handle 16 and on/off switch 22. Penetrator assembly may include penetrator (not expressly shown) and a connector, for example a pentagonal connector 20 as shown in FIG. 3A. As shown in FIG. 3B, housing 12 encloses motor 30, power supply 32, for example four or more AA batteries, motor connecting wires 34 between power supply 32 and motor 30 and switch connecting wires 36 between on/off switch 22 and power supply 32. The power supply to the apparatus may be any suitable number of AA batteries or any other type of battery, a source of direct current, a source of alternating current or a source of air or gas power. The motor may be reciprocating or rotational. Thruster bearing 45, for example a washer, may be located adjacent to housing 12 where drill shaft 40 exits housing 12. Thruster bearing 45 prevents the thrust or penetration force of drilling from being placed on gear assembly 38 as penetrator is drilled into bone. FIG. 3C shows one embodiment of the invention where drill shaft 40 may be separated into two interdigitating pieces at 42 in order to allow the two ends of drill shaft 40 to slide in and out as bone is penetrated to avoid applying excessive force to a gear assembly.

In FIG. 3B gear assembly 38 is coupled to motor 30. Gear assembly 38 may be a reduction gear assembly such as that shown in FIG. 3B that functions to reduce the revolutions per minute (RPMs) between the motor and drill shaft 40 and to increase drill shaft torque. Depending on the type of motor employed in the invention, gear assembly may or not be of the reduction type.

Figure 4A:
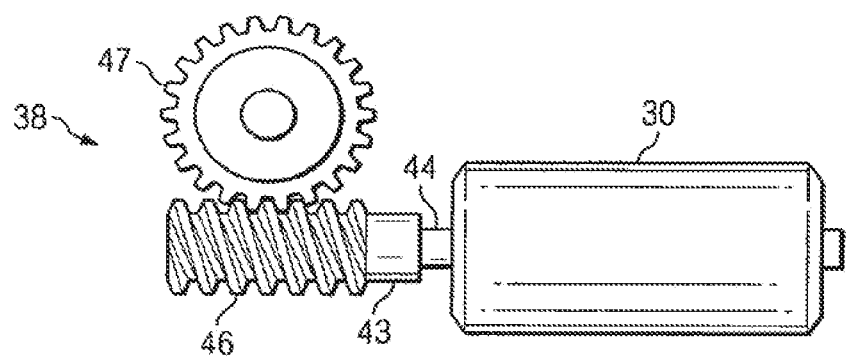
FIG. 4A-C illustrates various alternate embodiments of a reduction gear mechanism that may be included in an embodiment of the present invention.

By way of example and not limitation, a reduction gear assembly, for example a worm gear assembly is shown in more detail in FIG. 4A and may include first connector 43 that connects shaft 44 of motor 30 to worm gear 46. Worm gear 46 may engage spur gear 47. Reduction gear assembly 38 may be used to decrease the RPMs between the motor and penetrator assembly to provide an optimum RPM at the point of insertion of penetrator assembly into bone. Reduction gear assembly 38 may also be used to increase the torque of drill shaft and drilling power.

Figure 4B:
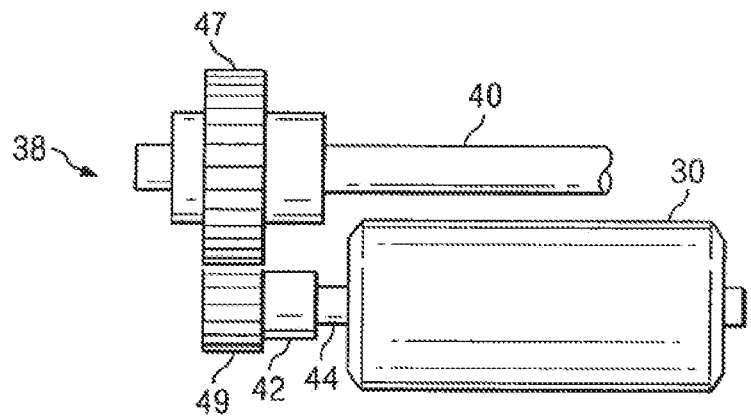
Figure 4C:
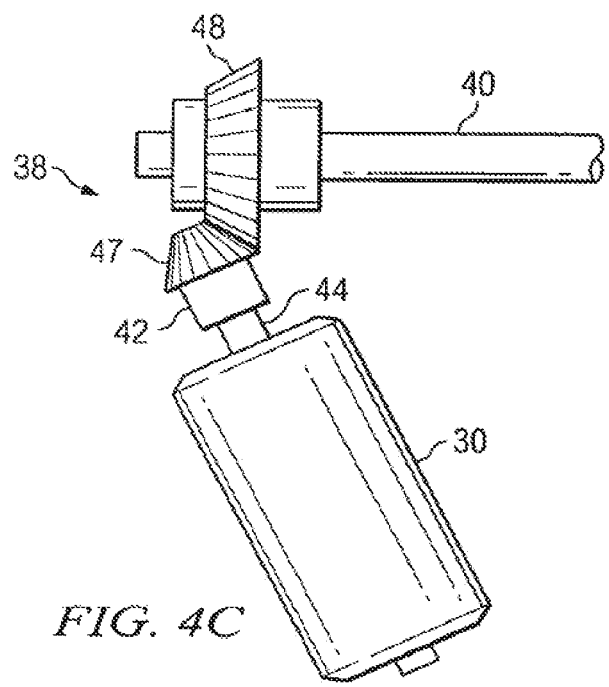

FIG. 4B illustrates one embodiment of reduction gear assembly 38 wherein a first spur gear 47 engages a second spur gear 49. FIG. 4C illustrates an alternate embodiment of reduction gear assembly 38 wherein spur gear 47 is offset from mitered gear 48 that may be preferable in some embodiments of the present invention. Other gears may be used in a reduction gear assembly, for example a planetary gear (not expressly shown) that may be used alone or in combination with a worm gear or a spur gear. In one embodiment of the current invention, gear assembly may be any suitable gear arrangement and is not limited to a reduction gear assembly.

FIGS. 5A-5C illustrate one embodiment of a penetrator assembly 55 operable to penetrate a bone marrow, having a removable inner trocar 50 and an outer penetrator 52. Also shown in FIG. 5A is a penetrator shield 26 that may be used to shield penetrator assembly 55 from inadvertent engagement and also serves to preserve needle sterility. In some embodiments outer penetrator 52 may be a type of needle or cannula, FIG. 5B illustrates outer penetrator 52 may include a male connecting piece 56 operable to engage a complementary female connecting piece 54 of inner trocar 50. Adjacent to male connecting piece 56 is connecting piece, locking mechanism 58 that locks into position on female connecting piece 54. Alternatively outer penetrator may include a female connecting piece suitable to engage a complementary male connecting piece of an inner trocar. Luer lock attachment 57 is coupled to male connecting piece 56 for connection to an intravenous tubing or syringe after the outer penetrator is positioned in the bone marrow. Male connecting piece 56 and female connecting piece 54 may also be of the luer-lock type. Inner trocar 50 includes stylet 53 that keeps outer penetrator 52 from getting plugged with debris created during drilling. Stylet 53 acts in combination with cannula portion 51 of outer penetrator. Outer penetrator 52 may include flange 60 that abuts or interfaces the skin of an insertion site and may be used to stabilize a penetrator assembly at the time of insertion. Penetrator assembly 55 may include various types of connectors, such as connector 62 that may be used to connect penetrator assembly 55 to a powered drill. Connector 62 may be pentagonal as shown in FIGS. 5A and 5C.

In one embodiment, the invention may include a specialized connector between the penetrator assembly and a powered drill. The connector performs at least two functions, a connecting function and a releasing function. The connecting function may be performed by various mechanisms such as a pentagonal male-female fitting or various lock-and-key mechanisms such as one that may include a combination or series of grooves and ridges or bars that match and interlock on a connector.

The releasing function may be performed by an O-ring connection, a magnetic connector, a chuck release mechanism, or a ball and detent mechanism with and without a spring. In one embodiment the releasing function may occur by means of a trigger mechanism whereby a trigger comes in contact with a holding mechanism and releases a penetrator or needle. In another embodiment a connecting mechanism may also include a trigger or retractable shield rod that slides up and contacts a holding mechanism or clamp that breaks away and releases a penetrator or needle after contact (not expressly shown).

Figure 6A:
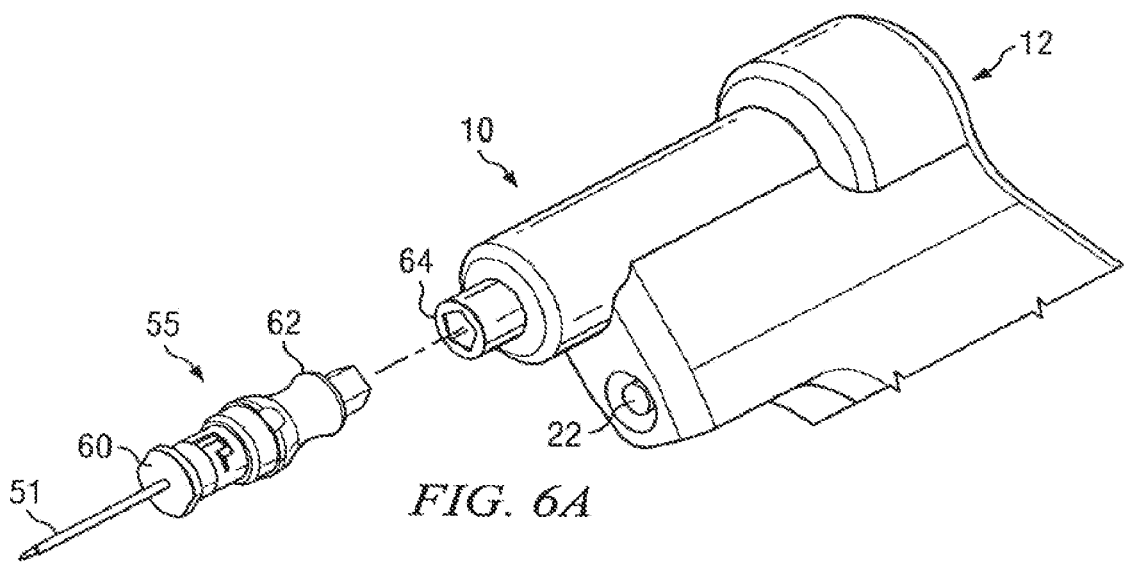
FIGS. 6A-C illustrate various alternate embodiments of a penetrator assembly connector of the present invention.
Figure 6B:
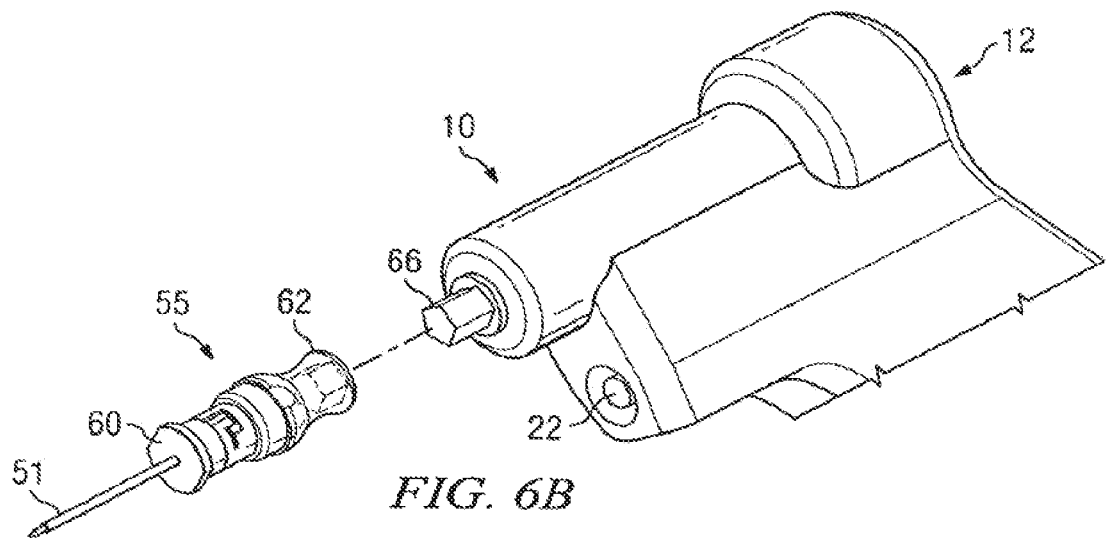
Figure 6C:
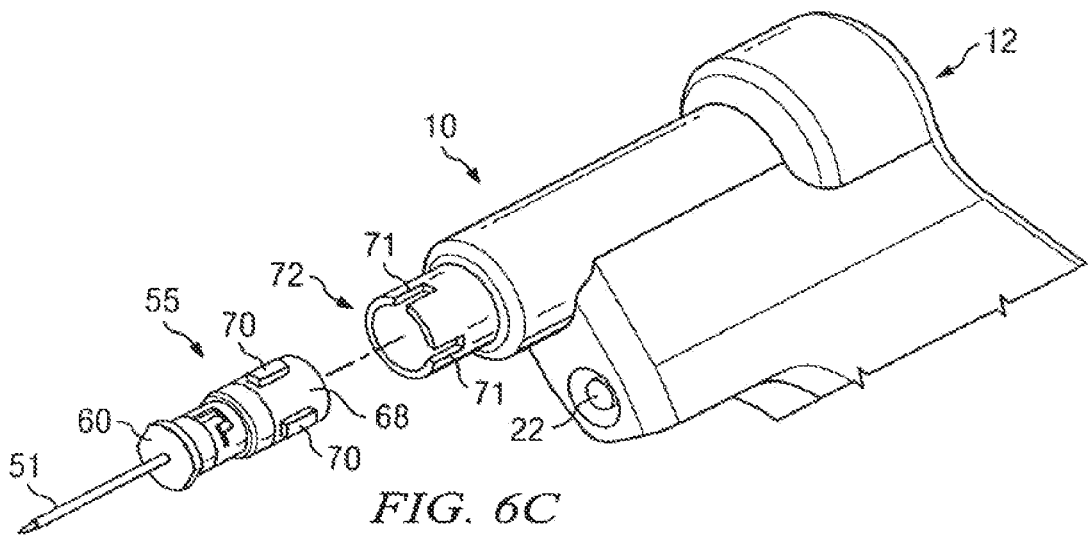

FIGS. 6A-C illustrate alternate embodiments of connectors operable to releasably attach penetrator assembly 55 to powered drill apparatus 10. FIG. 6A illustrates penetrator assembly connector 62 wherein connector 62 is formed to fit into a connector receptacle 64 and releasably lock into place. In this example, connector 62 and connector receptacle 64 are pentagonal shaped. Advantages of this embodiment may be the ease of attachment and removal of penetrator assembly 55 from powered drill apparatus 10. Penetrator assembly connector 62 may be formed from metal or plastic.

FIG. 6B illustrates an alternate embodiment of penetrator assembly connector wherein a female pentagonal receptacle 65 is operable to engage pentagonal connecting piece 66 attached to powered drill apparatus 1. FIG. 6C illustrates a further embodiment of a penetrator assembly connector wherein penetrator assembly connector 68 is a proprietary design having a pattern of ridges or bars 70 that engage a matching pattern of slots 71 on a connecting receptacle 72. Example penetrator assembly connectors may include any type of lock and key design or a pentagonal design. Penetrator assembly connectors of any type may be held in place by either a magnet, an O-ring connector or a ball and detent mechanism with or without a spring (not expressly shown).

In one embodiment, the penetrator assembly may include an outer penetrator such as a cannula, needle or hollow drill bit which may be of various sizes. Needles may be small (for pediatric patients), medium (for adults) and large (for oversized adults). Penetrator, cannulas or needles may be provided in various configurations depending on the clinical purpose for needle insertion. For example, there may be one configuration for administering drugs and fluids and an alternate configuration for sampling bone marrow or for other diagnostic purposes although one needle configuration may be suitable for both purposes. Needle configuration may vary depending on the site chosen for insertion of a needle.

FIGS. 7A-7D illustrate one embodiment of a penetrator assembly 80 that includes a removable inner trocar 82 and an outer penetrator 84. FIG. 7B illustrates a cross-sectional view of one embodiment of a penetrator assembly having a removable inner trocar 82 and an outer penetrator 84. Outer penetrator 84 includes flange 86 and flange groove 88. Flange 86 may be used to stabilize penetrator assembly 80 against the skin of an insertion site. Flange groove 88 is operable to engage plastic penetrator cover 94. The surface 85 of outer penetrator allows an operator to grasp the outer penetrator with two fingers and easily disengage the inner trocar 82 from outer penetrator 84. Outer penetrator 84 includes a penetrator cannula 96 that is hollow when stylet 100 is removed.

In FIG. 7C inner trocar 82 includes handle 98 that may have a surface 83 such as a series of discs formed along a longitudinal axis of the trocar, or a series of ridges or some other grasping means. Handle 98 allows an operator to easily grasp and manipulate inner trocar 82 and disengage it from outer penetrator 84. Inner trocar 82 also includes stylet 100. Stylet 100 exits an end of penetrator cannula 96 when inner trocar 82 is inserted into outer penetrator 84. Stylet 100 includes a cutting tip and is operable to penetrate bone marrow. In one embodiment of the invention, inner trocar 82 may include metal disc 95 to allow a magnetic connection between penetrator assembly and powered drill. Receptacle 97 may also engage a penetrator assembly male-type connector piece operable to connect penetrating assembly to a powered drill, or any other suitable connector.

Figure 7E:
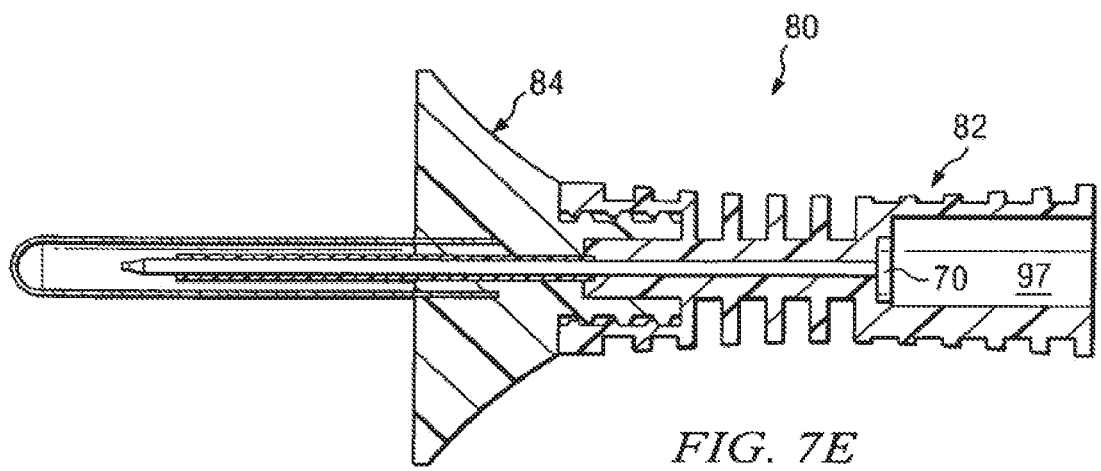
FIG. 7E-G illustrate examples of release mechanisms of the present invention.
Figure 7F:
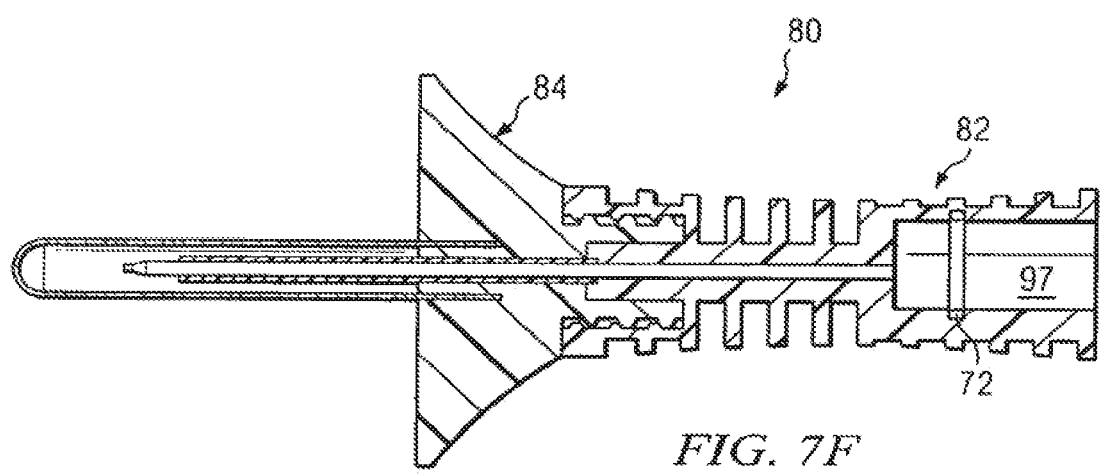
Figure 7G:
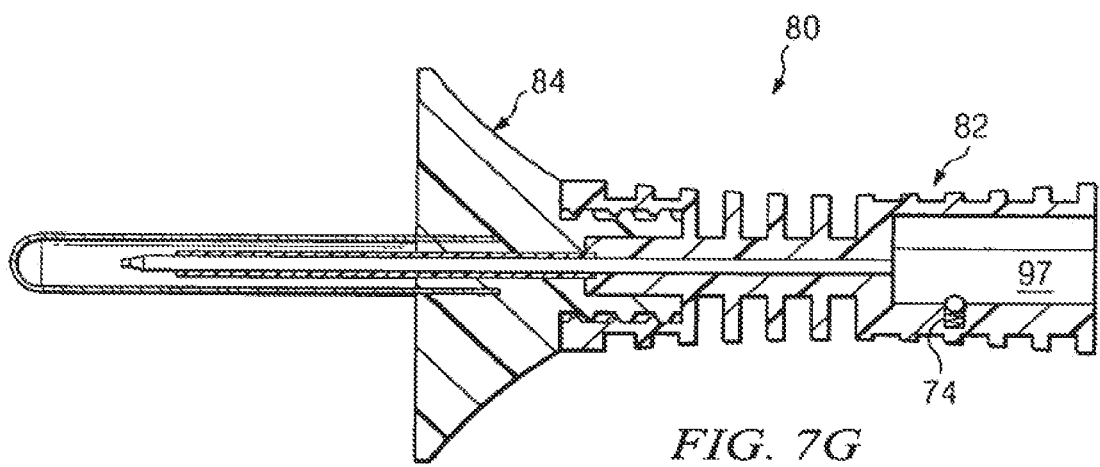

FIGS. 7E-7G illustrate example release mechanisms that may be coupled to a connector and included in penetrator assembly 80. FIG. 7E illustrates one embodiment of a magnetic release mechanism where magnetic disc 70 is included in inner trocar 82. In this embodiment magnetic disc 70 is at the base of open area or receptacle 97. In alternative embodiments a magnetic disc could be included with a pentagonal connector or a lock and key connector or any other suitable connector.

FIG. 7F illustrates another embodiment of a release mechanism where O-ring 72 is included in trocar 98 as part of a connector. In this embodiment O-ring 72 is in the wall of receptacle 97. O-ring 72 is able to engage a lock and key connector, a pentagonal connector or any other suitable connector.

FIG. 7G illustrates yet another embodiment of a release mechanism using ball and detent mechanism 74. In this embodiment ball and detent mechanism 74 is in the wall of receptacle 97. Ball and detent mechanism 74 is able to engage a lock and key connector, a pentagonal connector or any other suitable connector.

Figure 8A:
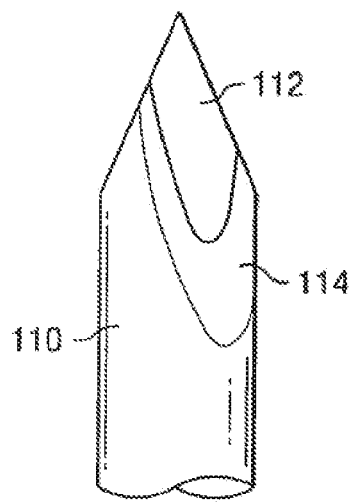
FIG. 8A illustrates one embodiment of a tip of a penetrator assembly of the present invention.

FIG. 8A illustrates an embodiment of an outer penetrator needle 110 and inner stylet 112. Cutting tip 114 of outer penetrator needle 110 and tip of inner stylet 112 are operable to penetrate bone marrow. In one embodiment of the invention the outer penetrator needle and the inner stylet are ground together as one unit in the manufacturing process to ensure that the two pieces are an exact fit and act as a single drilling unit.

Figure 8B:
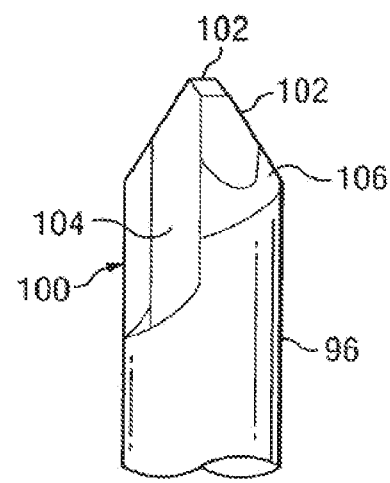
FIG. 8B illustrates one embodiment of a tip of a penetrator assembly of the present invention.

FIG. 8B illustrates another embodiment of an outer penetrator needle 96 and an inner stylet 100. Cutting tip 102 of inner stylet 100 is operable to penetrate bone marrow. Inner stylet may also include a longitudinal groove 104 that runs along the side of stylet 100 that allows bone chips and tissue to exit an insertion site as a penetrator assembly is drilled deeper into bone. Outer penetrator or needle 96 includes cutting tip 106 that facilitates insertion of outer penetrator or needle 96 and minimizes damage to outer penetrator or needle 96 as penetrator assembly 55 is inserted into bone marrow. In one embodiment of the invention the outer penetrator needle and the inner stylet are ground together as one unit in the manufacturing process to ensure that the two pieces are an exact fit and act as a single drilling unit.

Figure 9:
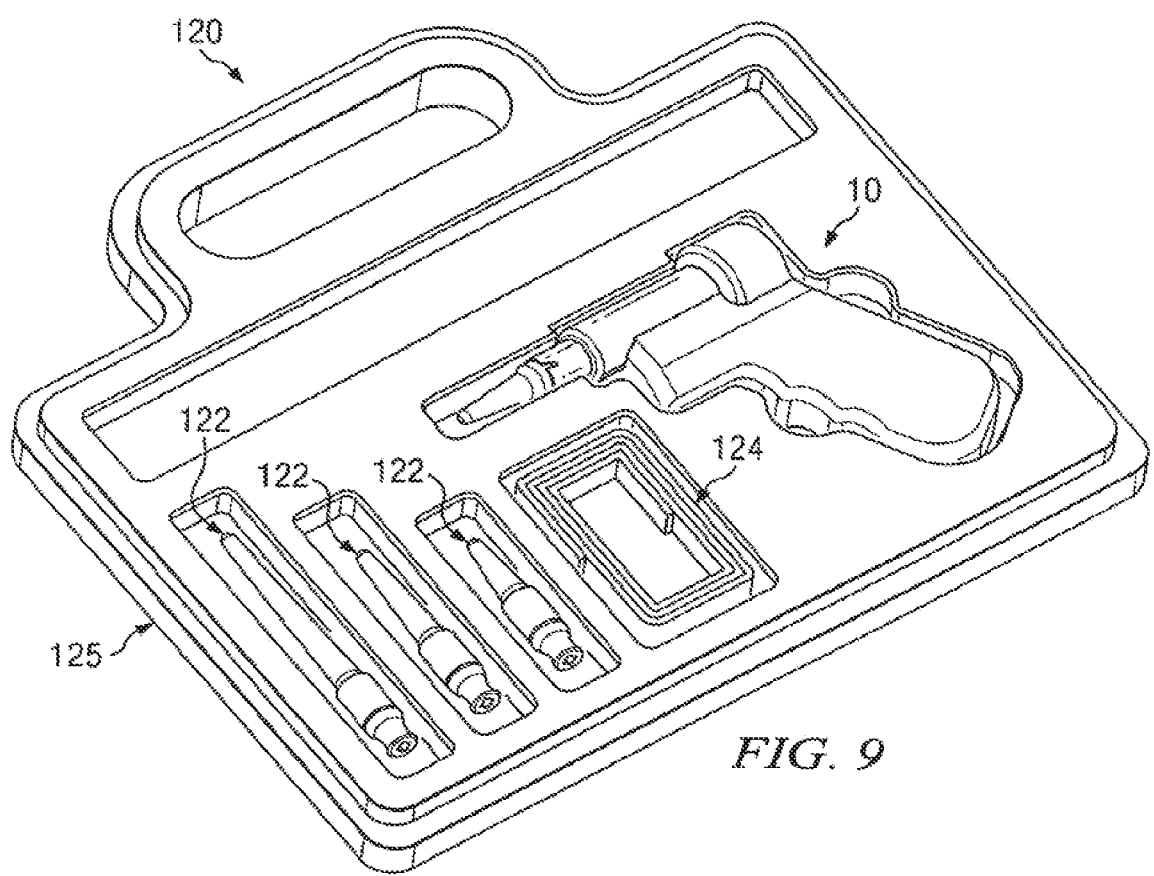
FIG. 9 illustrates one embodiment of a kit to access the bone marrow of the present invention.

FIG. 9 illustrates one embodiment of kit 120 to penetrate bone marrow Kit 120 includes apparatus 10 for penetrating bone marrow, alternative sizes of penetrator assemblies 122, and strap 124 suitable to immobilize an outer penetrator on an extremity during insertion of penetrator assembly 122. Carrying case 125 is also included.

Figure 10:
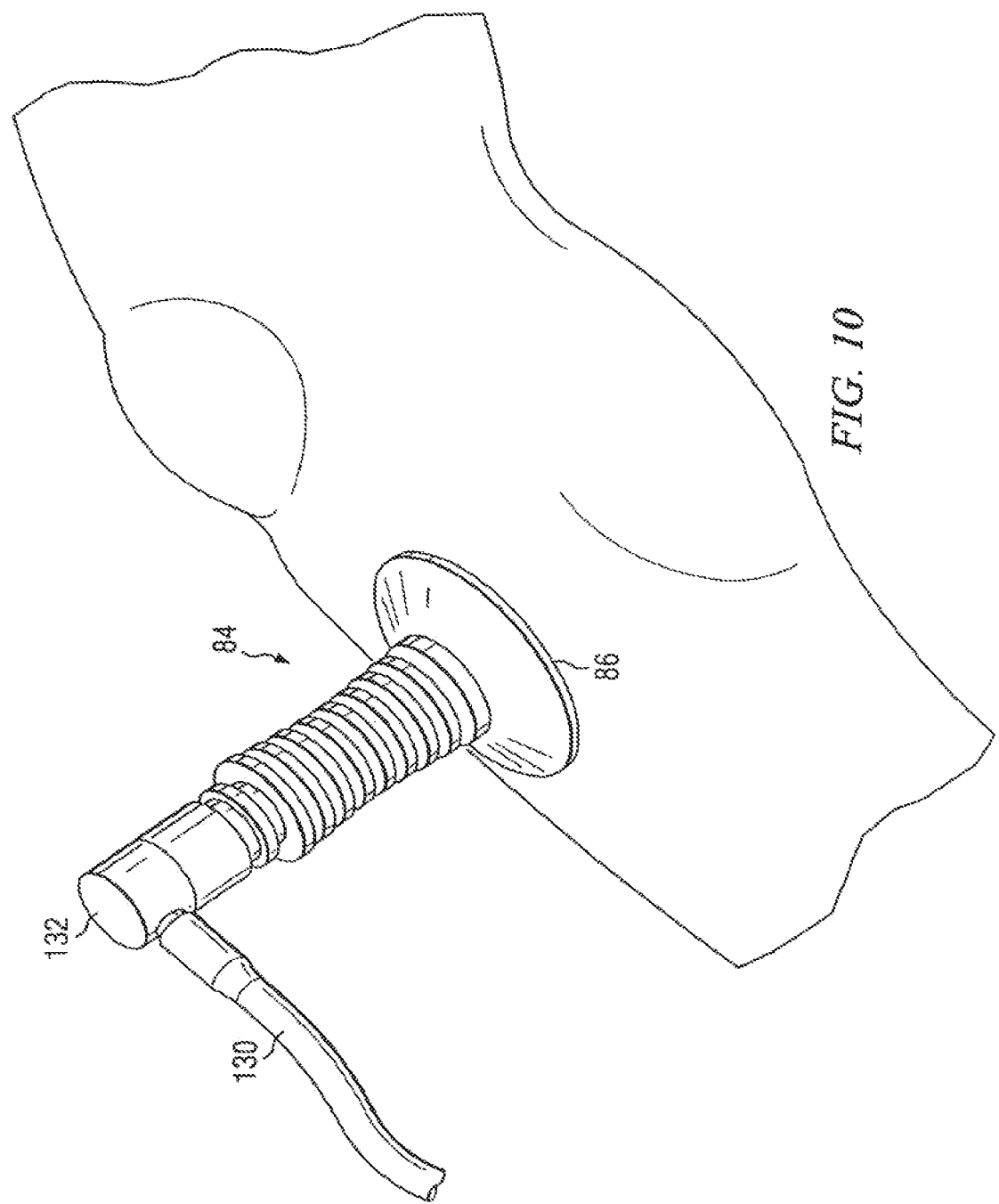
FIG. 10 illustrates one embodiment of a connector to attach to an outer penetrator of the present invention.

Once an outer penetrator or needle is inserted into a bone, it may be connected to a source of intravenous fluids or medication. FIG. 10 illustrates an example of a connector that may be used to connect the outer penetrator of a penetrator assembly to tubing 130, for example an intravenous tubing for providing intravenous fluids or medications to a person. Outer penetrator 84 is inserted into the bone marrow of an extremity. Right angle connector 132 is then used to connect intravenous tubing 130 to outer penetrator 84. Right angle connector has the advantage of allowing tubing to be connected to an outer penetrator or needle at an angle that will not kink or pinch off the lumen of the tubing. Other connectors or adapters may also be used to connect an outer penetrator to an intravenous tubing, another kind of tubing or to a syringe for use in providing medication or fluids to a person or for use in withdrawing a sample of blood from the bone marrow.

A method for providing access to the bone marrow includes using a powered drill, capable of reciprocal or rotational motion, to insert a penetrator assembly that includes an outer penetrator and an inner trocar into a bone marrow cavity. The powered drill is then released from the penetrator assembly and the inner trocar is grasped and removed from the outer penetrator. A connector present on the end of the outer penetrator, for example a luer lock connector, is then available for attachment to either an adapter, such as a right angle connector or directly to an intravenous tubing or syringe.

Although the present invention and its advantages have been described in detail, it should be understood that various changes, substitutions and alternations can be made herein without departing from the spirit and scope of the invention as defined by the following claims.

What is claimed is:

1. An apparatus for penetrating a bone and a bone marrow comprising:
   a housing enclosing a motor, a reduction gear assembly, a power supply, and a drill shaft;
   a penetrator assembly, operable to penetrate the bone marrow, having a removable inner trocar and an outer penetrator,
   the inner trocar including a stylet, a female connecting piece, and a penetrator assembly connector, and
   the outer penetrator including a cannula and a male connecting piece, the cannula of the outer penetrator configured to receive the stylet of the inner trocar, and the female connecting piece of the inner trocar configured to receive the male connecting piece of the outer penetrator;
   a connector operable to releasably attach the penetrator assembly to the drill shaft;
   the drill shaft operable to connect the penetrator assembly to the reduction gear assembly;
   the reduction gear assembly operable to engage and rotate the drill shaft;
   the motor operable to engage the reduction gear assembly and drive the penetrator into the bone marrow by rotation of the drill shaft; and
   the power supply operable to power the motor,
   wherein the penetrator assembly connector of the inner trocar is operable to attach the penetrator assembly to the connector, the inner trocar comprising a metal disc configured to magnetically engage the penetrator assembly with the connector.

2. The apparatus of claim 1, wherein the releasable connector comprises a pentagonal connector coupled to a release mechanism.

3. The apparatus of claim 1, wherein the reduction gear assembly comprises a first shaft attached to a gear operable to engage at least one other gear.

4. The apparatus of claim 1, wherein the reduction gear assembly comprises a planetary gear.

5. The apparatus of claim 1, the penetrator assembly trocar comprising a tip having a longitudinal groove operable to release bone chips from an insertion site as the penetrator assembly is drilled into the bone marrow and the penetrator assembly outer penetrator having a cutting edge.

6. The apparatus of claim 1, wherein the power supply comprises a power supply from the group:
   (i) a plurality of batteries;
   (ii) a source of direct current;
   (iii) a source of alternating current;
   (iv) at least one rechargeable battery.

7. The apparatus of claim 1, wherein the motor is from the group:
(i) gas-powered;
(ii) a reciprocating motor;
(iii) a rotational motor.

8. The apparatus of claim 1, wherein the drill shaft comprises a first end operable to interdigitate with a second end of the drill shaft.

9. The apparatus of claim 1, wherein the housing includes a thruster bearing.

10. The apparatus of claim 1, wherein the outer penetrator is operable to attach to an intravenous extension tube.

11. The apparatus of claim 1, wherein the outer penetrator is operable to connect to a right angle connector.

12. The apparatus of claim 1, wherein the reduction gear assembly comprises a first shaft attached to a worm gear operable to engage at least one other gear.

13. The apparatus of claim 1, wherein the reduction gear assembly is offset at an angle relative to the motor.

14. The apparatus of claim 1, wherein the drill shaft comprises a thruster bearing.

15. The apparatus of claim 1, operable to provide access to a bone marrow wherein: the outer penetrator has a flange operable to engage an insertion site proximate the bone marrow; and the inner trocar is operable to releasably engage the connector.

16. The apparatus of claim 15, wherein the outer penetrator is operable to connect to a source of intravenous fluids or medication by means of a right angle connector.

\* \* \* \* \*